US012285262B2

(12) United States Patent
Farah et al.

(10) Patent No.: US 12,285,262 B2
(45) Date of Patent: Apr. 29, 2025

(54) EVOKED RESPONSE PROBE AND METHOD OF USE

(71) Applicant: Alpha Omega Engineering Ltd., Nof HaGalil (IL)

(72) Inventors: Maroun Farah, Nazareth (IL); Hagai Bergman, Jerusalem (IL)

(73) Assignee: Alpha Omega Engineering Ltd., Nof HaGalil (IL)

( * ) Notice: Subject to any disclaimer, the term of this patent is extended or adjusted under 35 U.S.C. 154(b) by 42 days.

(21) Appl. No.: 16/424,528

(22) Filed: May 29, 2019

(65) Prior Publication Data

US 2019/0274572 A1    Sep. 12, 2019

Related U.S. Application Data

(63) Continuation of application No. 14/475,223, filed on Sep. 2, 2014, now Pat. No. 10,327,663.

(Continued)

(51) Int. Cl.
*A61B 5/377* (2021.01)
*A61B 5/00* (2006.01)
(Continued)

(52) U.S. Cl.
CPC .............. *A61B 5/377* (2021.01); *A61B 5/293* (2021.01); *A61B 5/6868* (2013.01); *A61B 46/00* (2016.02); *A61B 5/6814* (2013.01)

(58) Field of Classification Search
CPC ........... A61B 5/24; A61B 5/291; A61B 5/377; A61B 5/6814; A61B 5/6868; A61B 46/00;
(Continued)

(56) References Cited

U.S. PATENT DOCUMENTS

| 3,263,680 A | 8/1966 | Morgan |
| 5,843,093 A | 12/1998 | Howard, III |

(Continued)

FOREIGN PATENT DOCUMENTS

| WO | WO 2008/054312 | 5/2008 |
| WO | WO 2016/060749 | 4/2016 |

OTHER PUBLICATIONS

International Preliminary Report on Patentability Dated Mar. 16, 2017 From the International Bureau of WIPO Re. Application No. PCT/US2015/048169. (7 Pages).

(Continued)

*Primary Examiner* — Christopher A Flory

(57) ABSTRACT

A therapeutic effect assessment system, including:
  a probe shaped and sized to be inserted into a brain of a subject, having a proximal end and a distal end and a longitudinal axis, the probe including a plurality of contacts operably coupled thereto, disposed along the longitudinal axis, wherein the probe is selectively operable for stimulating an electrophysiological evoked responses;
  at least one electrode configured to record readings of evoked responses caused by the stimulating; and
  an analysis module electrically connected to the probe and to the at least one electrode, wherein the analysis module is configured to transform or reduce certain parameters from the recorded readings of evoked responses in order to identify a threshold of brain stimulation that produces a therapeutic effect.

14 Claims, 12 Drawing Sheets

Related U.S. Application Data

(60) Provisional application No. 61/872,672, filed on Aug. 31, 2013, provisional application No. 61/872,675, filed on Aug. 31, 2013.

(51) Int. Cl.
*A61B 5/293* (2021.01)
*A61B 46/00* (2016.01)

(58) Field of Classification Search
CPC ....... A61B 6/293; A61B 6/377; A61B 6/6814; A61B 6/6868
See application file for complete search history.

(56) References Cited

U.S. PATENT DOCUMENTS

| | | | |
|---|---|---|---|
| 6,102,044 A | 8/2000 | Naidyhorski | |
| 6,129,685 A | 10/2000 | Howard, III | |
| 6,263,225 B1 | 7/2001 | Howard, III | |
| 6,463,328 B1 | 10/2002 | John | |
| 6,480,743 B1* | 11/2002 | Kirkpatrick | A61N 1/36135 |
| | | | 607/45 |
| 6,840,117 B2 | 1/2005 | Hubbard, Jr. | |
| 7,077,822 B1 | 7/2006 | Howard, III | |
| 7,089,059 B1* | 8/2006 | Pless | A61B 5/6864 |
| | | | 607/45 |
| 7,209,787 B2 | 4/2007 | DiLorenzo | |
| 7,582,062 B2 | 9/2009 | Magill et al. | |
| 7,951,181 B2 | 5/2011 | Ahadevan-Jansen et al. | |
| 8,280,514 B2* | 10/2012 | Lozano | A61B 5/6864 |
| | | | 607/45 |
| 8,295,935 B2* | 10/2012 | Okun | A61N 1/36082 |
| | | | 607/45 |
| 8,792,972 B2 | 7/2014 | Zaidel et al. | |
| 8,849,392 B2 | 9/2014 | Lozano | |
| 9,265,965 B2 | 2/2016 | Fox et al. | |
| 9,387,319 B2 | 7/2016 | Pianca | |
| 9,604,056 B2 | 3/2017 | Starr et al. | |
| 10,765,370 B2* | 9/2020 | Toth | A61B 5/4875 |
| 11,357,986 B2 | 6/2022 | Steinke et al. | |
| 2002/0188330 A1* | 12/2002 | Gielen | A61B 5/377 |
| | | | 607/45 |
| 2003/0149450 A1* | 8/2003 | Mayberg | A61P 9/00 |
| | | | 607/3 |
| 2004/0019370 A1* | 1/2004 | Gliner | A61N 1/36017 |
| | | | 607/48 |
| 2004/0049121 A1 | 3/2004 | Yaron | |
| 2004/0097802 A1 | 5/2004 | Cohen | |
| 2004/0199235 A1 | 10/2004 | Younis | |
| 2004/0215260 A1* | 10/2004 | Vonk | A61N 1/3706 |
| | | | 607/11 |
| 2004/0249422 A1* | 12/2004 | Gliner | A61N 1/36067 |
| | | | 607/58 |
| 2005/0065427 A1 | 3/2005 | Magill et al. | |
| 2005/0182456 A1 | 8/2005 | Ziobro et al. | |
| 2005/0267356 A1 | 12/2005 | Ramasubramanian et al. | |
| 2006/0173510 A1 | 8/2006 | Besio et al. | |
| 2006/0217781 A1* | 9/2006 | John | A61N 1/36017 |
| | | | 607/45 |
| 2006/0252976 A1* | 11/2006 | Rosero | A61N 1/372 |
| | | | 600/2 |
| 2006/0276719 A1* | 12/2006 | Litvak | A61B 5/24 |
| | | | 600/544 |
| 2006/0276722 A1* | 12/2006 | Litvak | A61B 5/7217 |
| | | | 600/554 |
| 2006/0287566 A1 | 12/2006 | Zangen et al. | |
| 2007/0043268 A1 | 2/2007 | Russell | |
| 2007/0043401 A1 | 2/2007 | John | |
| 2007/0067003 A1* | 3/2007 | Sanchez | A61N 1/36082 |
| | | | 607/45 |
| 2007/0129770 A1* | 6/2007 | Younis | A61N 1/0534 |
| | | | 607/45 |
| 2007/0142874 A1* | 6/2007 | John | A61N 2/006 |
| | | | 607/45 |
| 2007/0197892 A1* | 8/2007 | Shen | A61N 1/0529 |
| | | | 600/378 |
| 2007/0239059 A1 | 10/2007 | McIver | |
| 2008/0004904 A1 | 1/2008 | Tran | |
| 2008/0027346 A1 | 1/2008 | Litt et al. | |
| 2008/0027504 A1* | 1/2008 | Bedenbaugh | A61N 1/0536 |
| | | | 607/45 |
| 2008/0045775 A1* | 2/2008 | Lozano | A61N 1/36082 |
| | | | 600/12 |
| 2008/0103547 A1* | 5/2008 | Okun | A61N 1/0534 |
| | | | 607/45 |
| 2009/0099622 A1* | 4/2009 | Fowler | A61N 1/36082 |
| | | | 607/45 |
| 2009/0105786 A1* | 4/2009 | Fetz | A61N 1/36103 |
| | | | 607/48 |
| 2009/0131995 A1* | 5/2009 | Sloan | A61N 1/0529 |
| | | | 607/3 |
| 2009/0318779 A1 | 12/2009 | Tran | |
| 2009/0319001 A1 | 12/2009 | Schiff | |
| 2009/0326627 A1 | 12/2009 | Moffitt et al. | |
| 2010/0036230 A1 | 2/2010 | Greene et al. | |
| 2010/0241020 A1 | 9/2010 | Zaidel et al. | |
| 2010/0280334 A1 | 11/2010 | Carlson et al. | |
| 2010/0280335 A1 | 11/2010 | Carlson et al. | |
| 2010/0280574 A1 | 11/2010 | Carlson et al. | |
| 2010/0280579 A1 | 11/2010 | Denison et al. | |
| 2010/0292758 A1 | 11/2010 | Lee et al. | |
| 2010/0298907 A1* | 11/2010 | Lombardi | A61N 1/37247 |
| | | | 607/45 |
| 2011/0115624 A1 | 5/2011 | Tran | |
| 2011/0171325 A1 | 7/2011 | Lozano | |
| 2011/0264165 A1 | 10/2011 | Molnar et al. | |
| 2011/0288365 A1 | 11/2011 | Zangen et al. | |
| 2011/0288400 A1 | 11/2011 | Russell et al. | |
| 2011/0288619 A1 | 11/2011 | Pianca | |
| 2011/0307030 A1 | 12/2011 | John | |
| 2012/0046710 A1 | 2/2012 | DiGiore et al. | |
| 2012/0065699 A1* | 3/2012 | Bedenbaugh | A61N 1/0534 |
| | | | 607/45 |
| 2012/0078327 A1* | 3/2012 | Sloan | A61N 1/37205 |
| | | | 607/72 |
| 2012/0092157 A1 | 4/2012 | Tran | |
| 2012/0095352 A1 | 4/2012 | Tran | |
| 2012/0101552 A1 | 4/2012 | Lazarewicz et al. | |
| 2012/0165634 A1* | 6/2012 | Lee | A61B 5/00 |
| | | | 600/345 |
| 2012/0271375 A1* | 10/2012 | Wu | A61N 1/36153 |
| | | | 607/45 |
| 2012/0289869 A1 | 11/2012 | Tyler | |
| 2012/0289871 A1* | 11/2012 | Lozano | A61P 29/00 |
| | | | 601/84 |
| 2012/0303089 A1* | 11/2012 | Martens | A61N 1/36185 |
| | | | 607/45 |
| 2012/0310298 A1 | 12/2012 | Besio et al. | |
| 2012/0330109 A1 | 12/2012 | Tran | |
| 2013/0009783 A1 | 1/2013 | Tran | |
| 2013/0013030 A1* | 1/2013 | Mahadevan-Jansen | A61N 5/0622 |
| | | | 607/89 |
| 2013/0066394 A1* | 3/2013 | Saab | A61N 1/36171 |
| | | | 607/46 |
| 2013/0066395 A1 | 3/2013 | Simon et al. | |
| 2013/0178692 A1 | 7/2013 | Zangen et al. | |
| 2013/0197424 A1* | 8/2013 | Bedenbaugh | A61N 1/0534 |
| | | | 604/20 |
| 2013/0211291 A1 | 8/2013 | Tran | |
| 2014/0018894 A1 | 1/2014 | Moffitt et al. | |
| 2014/0074176 A1* | 3/2014 | Jansen | A61N 5/0622 |
| | | | 607/3 |
| 2014/0094823 A1 | 4/2014 | Carcieri et al. | |
| 2014/0104059 A1 | 4/2014 | Tran | |
| 2014/0107728 A1 | 4/2014 | Fried et al. | |
| 2014/0163627 A1* | 6/2014 | Starr | A61N 1/0531 |
| | | | 607/3 |
| 2014/0194945 A1* | 7/2014 | Stypulkowski | A61N 1/36185 |
| | | | 607/45 |

(56) References Cited

U.S. PATENT DOCUMENTS

| | | | |
|---|---|---|---|
| 2014/0236257 A1* | 8/2014 | Parker | A61B 5/4824 607/46 |
| 2014/0243714 A1* | 8/2014 | Ward | A61M 5/1723 601/2 |
| 2014/0249429 A1 | 9/2014 | Tran | |
| 2014/0249542 A1 | 9/2014 | Moffitt et al. | |
| 2014/0275926 A1 | 9/2014 | Scott et al. | |
| 2014/0324118 A1 | 10/2014 | Simon et al. | |
| 2014/0364721 A1* | 12/2014 | Lee | A61B 5/369 600/411 |
| 2015/0005680 A1 | 1/2015 | Lipani | |
| 2015/0065839 A1 | 3/2015 | Farah et al. | |
| 2015/0224326 A1 | 8/2015 | Toth et al. | |
| 2015/0231395 A1* | 8/2015 | Saab | A61B 5/4824 607/46 |
| 2015/0238104 A1* | 8/2015 | Tass | A61B 5/7246 600/409 |
| 2015/0297139 A1 | 10/2015 | Toth | |
| 2015/0335288 A1 | 11/2015 | Toth et al. | |
| 2015/0359467 A1 | 12/2015 | Tran | |
| 2016/0067494 A1 | 3/2016 | Lipani | |
| 2016/0074661 A1 | 3/2016 | Lipani | |
| 2016/0082180 A1 | 3/2016 | Toth et al. | |
| 2016/0106994 A1 | 4/2016 | Crosby et al. | |
| 2016/0121115 A1 | 5/2016 | Guillory et al. | |
| 2016/0287166 A1 | 10/2016 | Tran | |
| 2016/0346542 A1 | 12/2016 | Simon et al. | |
| 2016/0360965 A1 | 12/2016 | Tran | |
| 2017/0014630 A1 | 1/2017 | Fried et al. | |
| 2017/0120043 A1 | 5/2017 | John | |
| 2017/0120052 A9 | 5/2017 | Simon et al. | |
| 2017/0224990 A1 | 8/2017 | Goldwasser et al. | |

OTHER PUBLICATIONS

International Search Report and the Written Opinion Dated Feb. 9, 2016 From the International Searching Authority Re. Application No. PCT/US2015/048169.
Invitation to Pay Additional Fees Dated Nov. 2, 2015 From the International Searching Authority Re. Application No. PCT/US2015/048169.
Notice of Allowance Dated Feb. 12, 2019 From the US Patent and Trademark Office Re. U.S. Appl. No. 14/475,223. (11 pages).
Official Action Dated May 22, 2018 From the US Patent and Trademark Office Re. U.S. Appl. No. 14/475,223. (18 pages).
Restriction Official Action Dated Jul. 5, 2017 From the US Patent and Trademark Office Re. U.S. Appl. No. 14/475,223. (10 Pages).
Supplementary European Search Report and the European Search Opinion Dated May 11, 2018 From the European Patent Office Re. Application No. 15850741.8. (10 Pages).
Communication Pursuant to Article 94(3) EPC Dated Jul. 9, 2020 From the European Patent Office Re. Application No. 15850741.8. (7 Pages).
Communication Pursuant to Article 94(3) EPC Dated May 18, 2021 From the European Patent Office Re. Application No. 15850741.8. (6 Pages).
Abhang et al. "Technological Basics of EEG Recording and Operation of Apparatus", Introduction to EEG- and Speech-Based Emotion Recognition, Chap.2: 19-50, Dec. 2016.

* cited by examiner

EVOKED RESPONSE PROBE AND METHOD OF USE

RELATED APPLICATIONS

This application is a continuation of U.S. patent application Ser. No. 14/475,223, filed on Sep. 2, 2014, which claims the benefit of priority under 35 USC § 119(e) of U.S. Provisional Patent Application No. 61/872,675, filed on Aug. 31, 2013 and U.S. Provisional Patent Application No. 61/872,672, filed on Aug. 31, 2013. The contents of the above applications are all incorporated by reference as if fully set forth herein in their entirety.

FIELD AND BACKGROUND OF THE INVENTION

The disclosure is directed to a surgical cranial drape, probes for mapping brain of a subject and their methods of use. Specifically, the disclosure is directed to a sterile surgical cranial drape embedded with electrodes; probe systems for mapping brain regions using evoked electrophysiological responses; and their methods of use in combination or separately.

In recent years, patients or any subject undergoing a surgical procedure is generally at least partially covered by a surgical drape. The surgical procedure is often performed through a fenestration (which can be a window, slit, or other opening) in the drape. It is important for surgical draping to provide an aseptic field about the central operative area. It is common practice for many types of surgery to cover the patient and operating table with a sterile drape in such a way that only the portion of the body upon which surgery is to be performed is presented to the care provider. The drape should therefore conform to the contour of the operative area to ensure that a sterile surgical field is maintained throughout and until the procedure is completed.

Likewise, in many surgeries involving the central nervous system (CNS), electrodes can be used as part of the surgery to either/or monitor, treat, stimulate and diagnose the subject, or in certain circumstances, to conduct research. For example, the placement of intracranial strip and grid electrodes for recording cortical electrocorticography (ECoG) has become an important component in the workup of patients who are considered for respective epilepsy surgery. Those can be electroencephalography (EEG) electrodes recording. Also, intra-operative electromyographic monitoring of the lower cranial motor nerves (LCN IX-XII) in skull base surgery is done using electromyographic electrodes (EMG).

Moreover, electrophysiological monitoring of selected neural pathways of the brain, brainstem, spinal cord and peripheral nervous system has become mandatory in some surgery of the CNS where preventable neural injury can occur. Likewise electrodes may be used in any other invasive procedure requiring that could be assisted by somatosensory evoked potential measurement and mapping.

For example, in deep brain stimulation (DBS) done pre or intra surgery in respective epilepsy surgery, a deep electrode can be inserted to the brain and physiological response measured. Currently, the surgery is performed on awake patient in order to enable a treating physician to access patient's responses and evaluate positioning of the electrode based on known patterns, in order to reach a target area in the brain for electric stimulation or any other surgical treatment.

The positioning of the electrodes is important for reaching a specific target in the brain for diagnostic, research and healing purposes, e.g. for extra cellular or trans-cranial recording from the brain and the nervous system as well as in functional neurosurgery or other biological tissue samples.

Accordingly, there is a need for a sterile surgical cranial drape embedded with electrodes, together or separate with an electrode system for mapping brain regions using evoked electrophysiological responses that can be used on sedated patients during selected procedures.

SUMMARY OF THE INVENTION

In an embodiment, provided is a surgical drape comprising, a film having an upper surface area and a lower surface area, the film surfaces areas defining a border, the film configured to provide a sterile barrier; a plurality of electrodes operably coupled to said film, wherein at least one of said plurality of electrodes being in contact with a patient's organ, the electrode having redundant number of leads connecting the electrode to a signal processor; optionally a locator coupled to the upper film surface; and optionally, a sensor, a transducer, or their combination operably coupled to the film.

In another embodiment, provided herein is a method of obtaining electrophysiological signal from an area of interest on a patient in need thereof, comprising: providing a surgical drape comprising: a polymeric film having an upper surface area and a lower surface area, the film surfaces areas defining a border, the film configured to provide a sterile barrier; a plurality of electrodes operably coupled to said film, wherein at least one of said plurality of electrodes being in contact with a patient's area of interest; a locator coupled to the upper film surface; and optionally, a sensor, a transducer, or their combination operably coupled to the film, wherein each of the plurality of said electrodes comprises a redundant number of selectable electric leads configured to couple the electrode to a signal processor; using the locator, locating the drape over the area of interest and using at least one of said plurality of electrodes; fenestrating the film over the area of interest such that at least one of the electrical leads couples the electrode to a signal processor; and measuring electrophysiological characteristics in the area of interest.

In yet another embodiment, provided herein is a brain mapping system, comprising: a first probe having a proximal end and a distal end and a longitudinal axis, the probe comprising a plurality of contacts operably coupled thereto, disposed along the longitudinal axis, wherein at least one contact is selectively operable for stimulating physiological evoked response; recording said physiological evoked response, or both; a recording electrode; and an analysis module operative for providing segmentation of the brain into a plurality of physiologically active brain regions, the analysis module being in communication with the probe, wherein the stimulation takes place in a first region and recording of the evoked response takes place in a second region.

In an embodiment, provided herein is a method of mapping a plurality of physiologically functional brain regions in a subject, implementable in a system comprising a probe having a proximal end and a distal end and a longitudinal axis, the probe comprising a plurality of contacts operably coupled thereto disposed along the longitudinal axis, wherein at least one contact is selectively operable for stimulating physiological evoked response; recording said physiological evoked response, or both; a recording electrode; and an analysis module operative for providing segmentation of the brain into a plurality of physiologically active brain regions, the analysis module being in communication with the probe and the recording electrode, the method comprising: contacting the plurality of physiologically functional brain regions with at least one macro-electrode; selectively operating at least one electrode to stimulate a first physiologically active brain region to evoke physiological response; selectively operating at least one electrode to record the evoked response in a second brain region; using the analysis module, analyzing the evoked response from the second brain region; and based on the analysis of the evoked response, segmenting the brain to physiologically active regions, thereby mapping the brain.

In an embodiment, provided herein is a brain mapping probe, comprising a plurality of contacts, configured to selectively provide localized stimulation between at least two of the plurality of contacts, measure differential between at least two of the plurality of contacts, short at least two of the plurality of contacts, or a combination comprising one or more of the foregoing.

BRIEF DESCRIPTION OF THE SEVERAL VIEWS OF THE DRAWING(S)

The features of the surgical cranial drape, the macro-electrodes for mapping brain of a subject and their methods of use described herein will become apparent from the following detailed description when read in conjunction with the drawings, which are exemplary, not limiting, and wherein like elements are numbered alike in several figures and in which.

Figure 1:
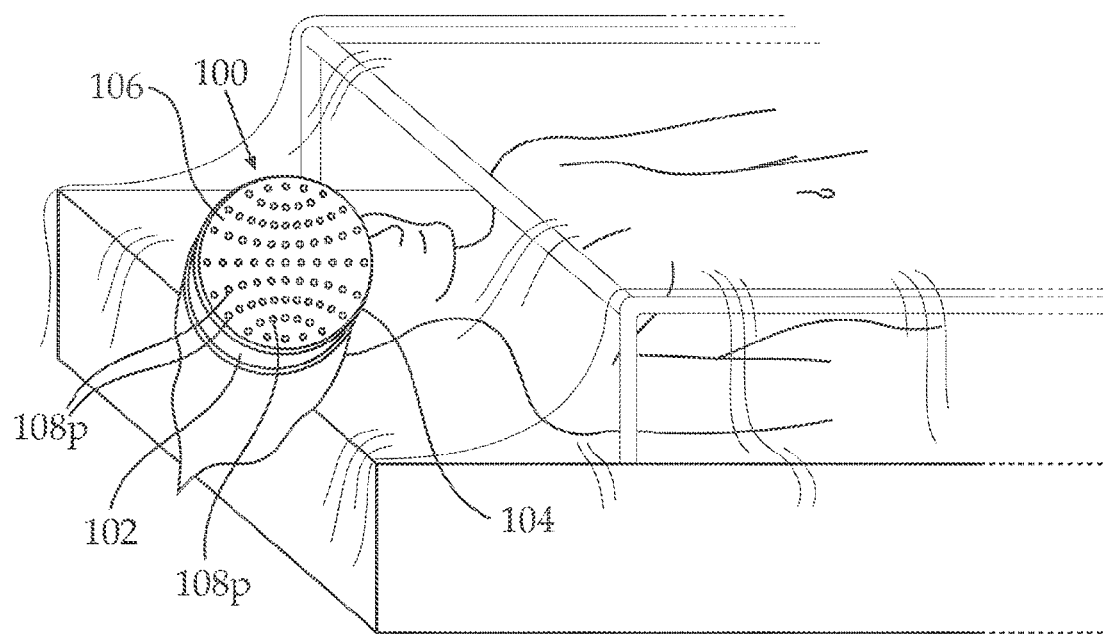
FIG. 1, illustrates an embodiment of an electrode carrying surgical drape constructed and operative in accordance with an embodiment of the present invention, when the surgical drape is partially mounted on a head of a patient.

While the disclosure is amenable to various modifications and alternative forms, specifics thereof have been shown by way of example in the drawings and will be further described in detail hereinbelow. It should be understood, however, that the intention is not to limit the disclosure to the particular embodiments described. On the contrary, the intention is to cover all modifications, equivalents, and alternatives.

DESCRIPTION OF SPECIFIC EMBODIMENTS OF THE INVENTION

The disclosure relates in one embodiment to sterile surgical cranial drapes embedded with electrodes, electrode systems for mapping brain regions using evoked electrophysiological responses and their methods of use in combination or separately.

Detailed embodiments of the present technology are disclosed herein; however, it is to be understood that the disclosed embodiments are merely exemplary, which can be embodied in various forms. Therefore, specific structural and functional details disclosed herein are not to be interpreted as limiting but merely as a basis for the claims and as a representative basis for teaching one skilled in the art to variously employ the present technology in virtually any appropriately detailed structure. Further, the terms and phrases used herein are not intended to be limiting but rather to provide an understandable and enabling description.

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the probe(s) includes one or more probe). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. Likewise, "first region" and "second region" are used to denote regions for stimulation and recording evoked potential (EP) and not necessarily define spatial arrangement. In other words, the first and second regions may be the same, adjacent or different brain region or region on the body of the subject where the systems and methods described herein are employed.

In addition, for the purposes of the present disclosure, directional or positional terms such as "top", "bottom", "upper," "lower," "side," "front," "frontal," "forward," "rear," "rearward," "back," "trailing," "above," "below," "left," "right," "horizontal," "vertical," "upward," "downward," "outer," "inner," "exterior," "interior," "intermediate," etc., are merely used for convenience in describing the various embodiments of the present disclosure.

In an embodiment, provided herein is a surgical drape comprising, a film having an upper surface area and a lower surface area, the film surfaces areas defining a border which provides a sterile barrier between the upper surface and the lower surface; a plurality of electrodes operably coupled to said film, wherein at least one of said plurality of electrodes being in contact with a patient's organ; a locator coupled to the film surface; and optionally, a sensor, a transducer, or their combination operably coupled to the film.

As used herein the term "film" can be used in a generic sense to include plastic web, regardless of whether it is film or sheet. Likewise, the term "laminate" when used in connection with the film, refers to a multiple-film composite structure having two or more films bonded together by any suitable means. The surgical drape described herein could accordingly be made from more than one layer (or even sides); whereby each layer can comprise wirings/conductors, as well as additional extra, or redundant connection to the electrodes. Moreover, another layer could be used for noise shielding (e.g. connected to a ground reference). for example: one layer could comprise electrode wiring with at least two wiring possibilities for each electrode running opposite posterior-anterior sides, while a second layer can be configured to include connection to each electrode having opposite diagonal and another layer with lateral-medial connections or leads. Each connection or lead could be selectively activated and the electrode can be operated with minimum or a single lead (or contact) communicating with the grid. Other layers can include an adhesive layer, an absorbent layer and the like.

The surgical drape described herein can have a polymeric film having two opposite surfaces, a first surface adapted to contact a patient skin and a second surface adapted to provide a sterile barrier, and a plurality of electrodes associated with the film, at least some (e.g., one or more) of the plurality of electrodes being in contact with patient skin.

As indicated, each of the plurality of electrodes can be provided with a redundant number of electrical leads (in other words, providing alternative wiring scheme), for example at least two separate independently selectable electrical leads extending in different directions from the electrode and maintain electronic communication (e.g., current, data, signal, etc.), the leads configured to operate independently. For example, the electrical leads can run in opposite posterior-anterior sides of the surgical drape, or be configured to include connection to each electrode having opposite diagonal, or in another example with lateral-medial connections or leads. Moreover, the conductors (in other words, leads or connectors) connecting the electrodes to a recording device (e.g., a transceiver) could be stretchable or resilient, and at the same time they do not cut. Accordingly and in an embodiment; in operations like a burhole operation where the fenestration in the drape is not that big, fenestration will not cut the wires, rather instead they will be moved according to the cut and according the stretch direction of the drape. Stretching could therefore be advantageous because there is a difference in the skull size between different people. The term "resilient" refers in an embodiment to the ability of the leads or contacts to resume their original shape or position after being compressed or deflected. A person holding ordinary skill in the art would readily recognize that any redundant lead coupled to the electrode at any angle is covered by the description provided.

The plurality of electrodes operably coupled to the film used in conjunction with the surgical drape described herein can be integrally formed within said film. For example, by using electroconductive ink, or, in another example, creating a flexible printed circuit board (PCB) and the like, or in another embodiment, the electrodes can be selectively removable from the film by, for example stitching or by using adhesive, or a combination thereof. The term "selectively" as used herein, refers to circumstances where the element or steps to which the term refers is activated or deactivated without affecting other elements or steps or the system's, apparatus' or method's final purpose.

It is also appreciated that any kind of medical electrode may be used. For example, EEG electrodes can be used, however it will be appreciated that any kind of medical electrodes comprising conducting contacts, for obtaining various physiological characteristics of a patient may be used in accordance to an embodiment of the present invention. These are, for example, EMG, EKG, ERP, EP, VEP, SSEP medical electrodes or a combination comprising one or more of the foregoing electrodes. Other sensors may be embedded similarly within the film (for example, as an electrode layer in a laminated film), used in conjunction with the surgical drape described herein, and can be for example; temperature sensors, (NIR e.g.) oxygen sensors, current sensors, and the like. Accordingly, the surgical drape described herein can further comprise a sensor array configured to provide additional information useful for the surgical operation.

A transceiver may be provided and used in conjunction with the surgical drape described herein, which can be adapted to communicate with each of the plurality of the electrodes in either a wired or a wireless manner. In case of a wireless communication, each of the plurality of electrodes can be configured to communicate its positioning to the transceiver via RF transmitter, utilizing Bluetooth, ZigBee or any other suitable wireless protocol.

The surgical (cranial) drape described herein, can be provided with marking that will allow the care provider to align and place the sterile drape on the patient head so that location of bur hole and/or EEG electrodes are set according to these markings. Accordingly, the positioning markings that will state the names of, for example the EEG electrodes according to known EEG systems e.g. the international 10-20 EEG system. Having the marking, or the electrodes disposed according to the 10-20 system will be maintained using the flexible or stretchable film material described herein and can for example be implementable using the resilient leads or contacts described herein.

The upper or lower surface of the film used in conjunction with the surgical drape described herein can further comprise a posterior locator coupled to the film upper or lower surfaces via a strip, configured to extend from the film's upper and/or or lower surfaces, an anterior locator coupled to the film upper or lower surfaces via a strip, configured to extend from the film's upper and/or lower surfaces configured to be positioned along a nasion-inion line of the subject (sometimes, due to variability in the subject's head size, there is a need for a stretch) or between markings found along the line connecting nasion-inion points. Likewise, the film upper or lower surfaces used in conjunction with the surgical drape described herein can further comprise a lateral right locator coupled to the film upper or lower surfaces via a strip, configured to extend from the film upper or lower surfaces, a left lateral locator coupled to the film upper or lower surfaces via a strip, configured to extend from the film upper or lower surfaces area border configured to be positioned perpendicular to the nasion-inion line (some stretch might be necessarily) of the subject and between the right and left preauricular points or between markings found along the line connecting the right and left preauricular points. The locators (anterior, posterior and right and left laterals) can have tabs used to pull the locators from the surface (upper or lower) of the film. The tabs, when pulled, or in another embodiment, tore, can expose an adhesive layer or have a liner, which when separated from the locator, can be used to adhere the surgical drape (whether stretched or not) onto the subject's scalp. In addition, the film used in surgical drape provided herein, can have at least a portion that is transparent and enables the care provider to observe the scalp of the subject, or in another embodiment, any area where the surgical drape is to be used.

Accordingly, the drape extensions can be coupled to markings used when applying, for example the EEG 10-20 system, for example the nasion, inion, preauricular points or other cranial markings. In some embodiments, the care provider/physician can first apply and anchor the front extension to the nasion land mark then remove a strip liner running from the front anterior to the posterior part of the drape and expose an adhesive strip of the film forming the drape. The drape can then be stretched from the nasion landmark to the inion landmark and care provider will push along the drape part over the adhesive strip to attach it to the skin. Following locating the extension along the nasion-inion line, the two lateral extensions for the preauricular points can be peeled away from the upper surface and be attached by care provider. Additionally, means for removing the liners and exposing the adhesive layer, for example strings coupled to the peelable strips (or a tab on a scored strip or similar means) can be pulled by the care provider in order to remove the liner under a strip running between the left and the right preauricular points; care provider will then press along and above this strip to attach the adhesive drape firmly along this strip. After that the rest of the strings can be pulled in order to remove the remaining liner protecting the adhesive sides of the drape. And a care provider at this point can apply pressure over all cranial parts of the drapes in order to make sure that drape is attached firmly to the scalp, effectively forming an electrode helmet.

In an embodiment, the term "peelable" refers to securing in an impervious manner by adhesive bonding or sealing, enabling the manual separation, in normal use of the locator strips, of the two pieces secured in this way, without tearing them, meaning that the connection between the locator(s), be it by means of an adhesive, heat sealing, scoring, or other means, can be broken, disrupted or eliminated by manually urging the locator strip away from the upper film without compromising the integrity of the films.

In an embodiment, instead of four strip extensions for the standard markings, number of these extensions could be different; and other standard or specific markings (e.g., EEG 10-20 markings system) can be used. Also instead of these extensions the drape could attach to these markings without any extension from it as there can be markings on the drape to specify the anchoring points for the markings.

In an embodiment, the surgical drapes described herein, are used in methods for obtaining electrophysiological signal from an area of interest on. Accordingly and in an embodiment, provided herein is a method of obtaining electrophysiological signal from an area of interest on a patient in need thereof, comprising: providing a surgical drape comprising: a polymeric film having an upper surface area and a lower surface area, the film surfaces areas defining a border, the film configured to provide a sterile barrier; a plurality of electrodes operably coupled to said film, wherein at least one of said plurality of electrodes being in contact with a patient's area of interest; a locator coupled to the upper or lower film surfaces; and optionally, a sensor, a transducer, or their combination operably coupled to the film, wherein each of the plurality of said electrodes comprise at least two separate electrical leads (in other words, wires (e.g., resilient wires) covered (or uncovered) with an insulation used for conducting current between components such as the electrodes and a signal processor); using the locator, locating the drape over the area of interest and using at least one of said plurality of electrodes; fenestrating the film in the desired surgical access area near the area of interest; and measuring electrophysiological characteristics in the area of interest.

The term "coupled", including its various forms such as "operably coupled", "coupling" or "coupleable", refers to and comprises any direct or indirect, structural coupling, connection or attachment, or adaptation or capability for such a direct or indirect structural or operational coupling, connection or attachment, including integrally formed components and components which are coupled via or through another component or by the forming process (e.g., an electromagnetic field). Indirect coupling may involve coupling through an intermediary member or adhesive, or abutting and otherwise resting against, whether frictionally (e.g., against a housing) or by separate means without any physical connection.

The term "fenestration" or "fenestrating" refers to an opening provided through a surface of the film from the lower surface of the film to the upper surface of the film. A fenestration may have a variety of geometries for example; a straight cut, circular, semi-circular, oval, oblong, or cuts, incisions perforations and the like, having other geometries. In an embodiment, the drape undergoes fenestrating such that regardless of the size and shape of the cut, all electrodes are operational due to the redundant alternative wiring options. Likewise, following fenestration, resilient leads can be used to remove the obstructing leads from the fenestrated site without disrupting their operation.

The term "signal processor" as used herein refers in an embodiment, to a power source, a pre-amplifier, an amplifier, an A/D and/or D/A converter, or a module or system comprising one or more of the foregoing.

The step of locating in the methods described herein can further comprise peeling the anterior and posterior locators; pealing the right lateral locator and the left lateral locator;

positioning the anterior and posterior locator strips along the nasion-inion line of the patient; and positioning the left lateral and right lateral strips laterally above ears of the patient and perpendicular to the nasion-inion line between the left and right preauricular points.

In yet another embodiment, the surgical drape provided can be used together or separately with the brain mapping system described herein. Accordingly, provided herein is a brain mapping system, comprising: a first probe adapted to provide stimulation, recording or both recording and stimulation, having a proximal end and a distal end and a longitudinal axis, the probe comprising a plurality of contacts operably coupled thereto, disposed along the longitudinal axis, wherein at least one contact is selectively operable for stimulating physiological evoked response; recording said physiological evoked response, or both; an electrode; and an analysis module operative for providing segmentation of the brain into a plurality of physiologically active brain regions, the analysis module being in communication with the first probe, or electrode used for recording evoked response or both the probe and electrode.

Typically, in a sedated patient, most of physiological responses cannot be measured. However, in the brain mapping system provided herein, during the procedure of evoking response(s), the sedation/anaesthetic level of patient will be measured and recorded. The recorded evoked responses will be compared to the recorded sedation/anaesthetic level and then a determination would be made on whether or not to use the evoked responses, or alternatively, to normalize the recorded responses as a function of the sedation/anaesthetic level. Recording of the sedation/anaesthetic levels could be done by known methods for example by using EEG electrodes by analyzing the spatio-temporal patterns in the electroencephalogram (e.g., bispectral electroencephalographic monitoring) and then using special algorithms (e.g., Lempel-Ziv complexity analysis). Likewise, normalization could for example be done by dividing the evoked signals with the sedation/anaesthetic averaged level value at a certain window of time. Other normalization methods could be done as well. Accordingly and in an embodiment, the mapping system described herein can be used on sedated subjects.

The probe can comprise at least two different electrode types, the first type responsible for acute stimulation of at least one of the plurality of brain regions to evoke physiological responses or recording of the physiological evoked responses and the second type is being responsible for chronic stimulation of at least one of the plurality of brain regions. The brain mapping system can comprise a brain probe having a plurality of contacts, configured for placement in contact with the brain and operative for at least stimulating physiological evoked responses and/or recording the physiological evoked responses and analyzing module operative for identifying at least one characteristic of the brain.

In an embodiment, a functional map of functional brain regions of a patient is automatically created, using induction of physiological responses. This functional map represents either statistical segmentation of the brain into different brain regions, or provides for identification of a physiological characteristic of each of the plurality of brain regions. Further, the described mapping method is similarly applicable at any anatomical region during various surgical procedures, such as positioning a probe within patient's body to perform a biopsy, remove a cyst or for DBS surgeries. Stimulation of physiological responses can be performed, which provides for evoked physiological responses. These evoked physiological responses can be recorded and analyzed, in order to provide a functional map of different brain regions. The evoked physiological responses differ and this differentiation permits segmentation of the brain into different brain regions, thus as a result of the analysis of recorded evoked physiological responses, statistical segmentation of brain into different brain regions can be performed along the longitudinal axis of the brain probe. Alternatively, a characteristic of each of the brain regions is identified and recorded for further analysis.

The brain mapping system used in the methods of brain mapping described herein can also comprise at least one EEG electrode operative for at least one of stimulating the physiological evoked responses and recording the physiological evoked responses, or for example, ECoG electrode.

The probe used for both recording and/or stimulation, provided herein, can be, for example, comprising a plurality of contacts, configured to selectively provide localized stimulation between at least two of the plurality of contacts, measure differentially between at least two of the plurality of contacts, short at least two of the plurality of contacts, or a combination comprising one or more of the foregoing. The contacts can be arranged on the longitudinal axis of the probe and have a contact span ($C_S$, see e.g., FIG. 20), of between about 0.5 mm and about 2.5 mm, while insulation between adjacent contacts can have an insulation span (IS, see e.g., FIG. 20) of between about 0.25 mm and about 1.5 mm. In an embodiment, the total length of the probe is variable and can be between about 10 mm and about 1500 mm.

In another embodiment, the mapping probe can be comprised of alternating, selectively operable concentric and telescopically extendable electrodes separated by insulation tubes, where the same or different insulation spans ($I_S$) or contact spans ($C_S$) can be varied. The central probe, can be, for example a sharp tip (needle) that can be used for micro stimulating or macro recording.

Stimulating electrophysiological response and/or recording electrophysiological evoked response in the systems and methods described herein can comprise stimulating, recording or both stimulating and recording signals differentially, single ended or both differentially and single ended. For example, a differential sensing configuration can include a tip electrode used as the sensing electrode and a ring electrode used as a reference electrode. Typical tip-to-ring spacing can be approximately 10 mm but may be greater or less than 10 mm. Other differential sensing configurations using any type of available electrodes can be used. During differential sensing, both the sensing electrode and the reference electrode can be positioned along a mapped site, such as within a brain region or along a nerve branch, such that both electrodes are subjected to change in electrical potential caused by an electrophysiological event in the tissue.

Likewise, single ended sensing electrode configurations can comprise a sensing electrode in contact with a region of interest, paired with a reference electrode placed away from the region of interest such that the reference electrode is not subjected to changes in electrical potential caused by electrophysiological events occurring at the site. A reference electrode in a single ended configuration may be considered to be positioned far enough away from a signal source that it approximates a zero potential reference (conventionally defined as equivalent to a reference located at an infinite distance). Common single ended sensing configurations in the systems described herein can comprise a sensing electrode (or macro-contact) embodied as a tip or ring electrode (or contact) along a region of interest paired with a reference electrode. A sensing electrode may be any available tip, ring, or coil electrode. A reference electrode may be any available electrode implanted in a different region or implanted elsewhere in the body (e.g., along the arm), including subcutaneous electrodes.

Localized stimulation in the systems and methods described can be configured to be performed between two adjacent macro-contacts, for example a tip contact and a ring macro contact spaced between about 20 μm and about 500 μm from the tip contact (or electrode); recording evoked response, non-evoked response or both evoked and non-evoked response is configured to be performed by recording differential local field potential (LFP) between the two contacts, wherein one contact is a reference to the other.

At least two of the contacts in the systems and methods described can be macro or micro contacts and be configured and/or adapted to selectively perform localized stimulation, or non-localized stimulation. Unlike non-localized stimulation, in localized stimulation, the stimulation does not dissipate beyond the stimulating electrodes, because all the current that is run from one pole electrode will be received (or conducted) by (or through) the polar opposite contact and thus will only have a stimulation activation effect across these contact. Thus when current is conducted from certain contact and received by the other contact. Thus, the stimulation effect can be limited to the areas between these contacts and thus it will be localized to this area. Localized stimulation can be carried out using, for example, bipolar stimulation, whereby the contacts have different polarities (i.e. one is negative, one is positive) relative to each other, such that the current also runs between the stimulating electrodes, i.e. along or through the functional region sought to be mapped or classified, and because stimulation field in this configuration diminishes fast related to distance from contacts then thus the region activated by stimulation becomes narrower and the contacts provides more localized stimulation. Likewise, at least two of the contacts can be used to distinguish between various functional region in the brain of the subject by recording evoked response, non-evoked response or both evoked and non-evoked response field potentials, then based on predetermined threshold, calculate the difference between the field potentials to determine whether the region is uniform or should be clustered with other locations; short at least a pair of contacts; or be configured to select a combination of the foregoing. Effectively, the contacts systems described herein can be supported by as a system of switches that switches the electrode among the different conditions/states or modes of operation. Stimulation using the probe provided herein does not have to be only localized. For example, the contacts can be shorted and stimulation can be done through the shorted contacts. Shorting can be done by electrically coupling two or more contacts. Likewise, stimulation can be done using a single contact operating in a unipolar mode.

In an embodiment, the systems described herein, can be used in the methods for mapping a plurality of physiologically functional brain regions in a subject, comprising contacting the plurality of physiologically functional brain regions with at least one brain probe; selectively operating at least one electrode to stimulate a first physiologically functional brain region thereby evoking physiological response; selectively operating an electrode (which, in another embodiment, is coupled to the surgical drape provided herein), to record the evoked response in a second region; using the analysis module, analyzing the evoked response; and based on the analysis of the evoked response, segmenting the brain to physiologically functional regions, thereby mapping the brain. The first region and second region can be the same, adjacent or remote.

For example, electrodes (or contacts) of the probe can be used as both ES (Electrode-Stimulating) and ER (Electrode-Recording) electrodes. Accordingly, the brain probe can be configured to both stimulate the brain and evoke physiological responses and thereafter record the evoked responses. Or in other embodiment, the probe is used for localized stimulation only and recording of evoked response takes place in another region in the brain (for example, the cortex). Any number of brain probes may be used and placed apart at a varying distance or regions from each other. For example, the stimulation of the brain can be performed by stimulating brain probe (SBP) in the amygdala and recording of the evoked responses can be performed using EEG electrodes (Electroencephalogram) on the cortex, which can be positioned over the head of the patient. Opposite functionality can be similarly used, such that stimulation of physiological responses can be performed by TES (transcranial electrical stimulation) electrodes and recording of evoked responses can be performed by recording probe (RBP). Similarly, any number of EEG/TES electrodes may be used.

In an embodiment, the stimulation of the brain can be performed by stimulating brain probe (SBP) and recording of the evoked responses can be performed using ECoG electrodes (Electrocorticography), which can be positioned over the cortex of the patient. Likewise, opposite functionality can be similarly used, such that stimulation of physiological responses can be performed by ECoG electrodes and recording of evoked responses can be performed by RBP brain probe. Any number of ECoG electrodes may be used.

Moreover, stimulation of the brain can be performed by probe stimulating brain probe (SBP) and recording of the evoked responses can be performed using EMG electrodes (Electromyography), placed on (or in) muscles of the patient. Any number of EMG electrodes may be used. Further, the stimulation of the brain can be performed by TMS (Transcranial-Magnetic-Stimulation) and recording of the evoked responses can be performed using recording brain probe (RBP). The recording instrument, such as either RBP, MER, EEG, ECoG or EMG, can be configured to record evoked physiological responses in different body regions, which evoked physiological responses were previously inducted using a stimulation instrument, such as TES, SBP, EEG, ECoG or TMS. The method of mapping plurality of brain regions can comprise, for example the following steps: either fully inserting the brain probe into the brain in one step or incrementally advancing the probe through plurality of brain regions; stimulating plurality of brain regions to provide evoked physiological responses using at least one of the aforementioned stimulation methods (e.g., EMG); recording evoked physiological responses using at least one of the aforementioned recording methods (e.g., MER); analyzing recorded evoked physiological responses by an analyzing module.

The analyzing module preferably performs the following analysis: reduction of recorded evoked physiological responses into uni-dimensional or multi-dimensional parameters, measures or features; employing at least one of segmentation, clustering, classification, sorting, hidden Markov model or dynamic Bayesian network or a combination of the abovementioned analyses. As the result of the analysis performed by the analyzing module, segmentation or detection of different brain regions along the path of probe can be performed.

In addition, any kind of stimuli, such as visual, audial, muscle stimuli, transcranial magnetic stimulation, TES, tDCS, tACS, or electrical stimuli of the brain can evoke physiological responses, which can in turn be recorded by different means in different body regions, such as by means of brain probe, EEG ECoG, EMG, EKG, ERP, EP, VEP or SSEP medical electrodes.

Statistical evaluation used in the systems and methods described may employ at least one of the following algorithms for clustering, sorting, classification or detection of different brain regions: single link clustering; complete link clustering; average link clustering; K means algorithm; K prototypes algorithm; K medoids algorithm; Graph theoretic clustering; density based clustering algorithm and methods; template matching; threshold crossing; model based and neural networks; wavelet based algorithms or principal component analysis.

Example

During evoking of activity, stimulation electrodes are inserted in a first location (or region), and stimulation (localized or non-localized) is applied. Evoked activity is then recorded at a second location (or region).

Figure 21:
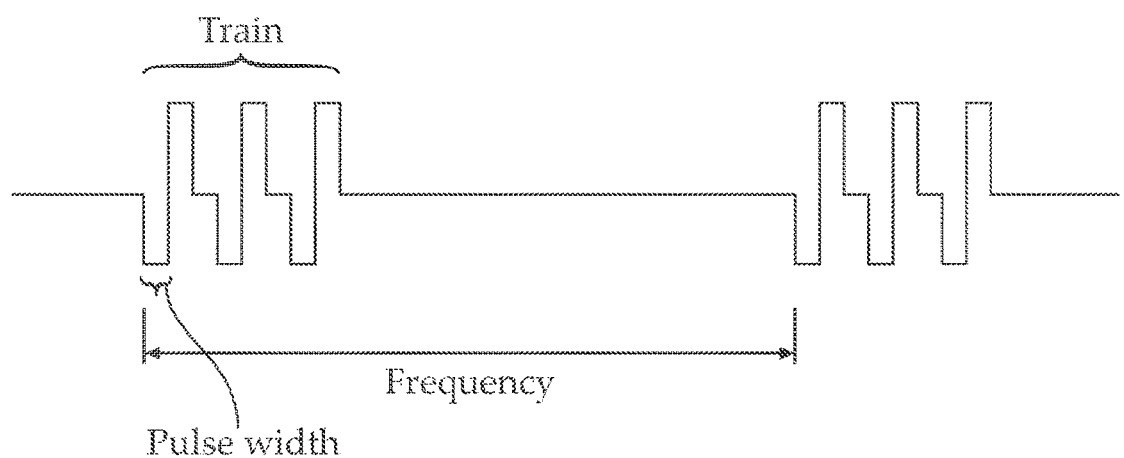
FIG. 21, shows an example of a stimulation protocol.

The following parameters establish the evoking protocol and the resulting evoked activity
   a. stimulation configuration (unipolar, bipolar, multi-polar); which is the stimulating electrode and which is the return electrode
   b. stimulation frequency
   c. stimulation trains (see e.g., FIG. 21)
   d. pulse width
   e. threshold values, amplitudes and another (e.g. temporal features)
   f. Pulse shape For example, if it is necessary to evoke activity in a certain location by stimulation in another location and there is no direct pathway between the two locations (or regions); e.g. the two locations are connected by more than one neural pathway, then in order to evoke useful physiological response stimulation is carried out using pulse trains (in other words, a series of pulses separated in time by a predetermined frequency, that can be the same or different along the pulse train). The number of pulses and their frequency in these trains are established to control the existence and features of the response. If there is a direct neural pathway (i.e. there are neurons connecting the two locations or regions and the activity is recorded from these neurons), then as an example number of pulses in stimulation trains are decreased and stimulation are conducted in the appropriate stimulation frequency that for example could be between 0.1-1000 Hz. In both conditions stimulation amplitude is also predetermined;

Stimulation threshold for the induction of electrophysiological recorded response activity is different from stimulation threshold for the induction of clinical functional effect. For recorded activity threshold; the minimal stimulation amplitude (or other value of the other important stimulation parameters) in a first location is sought, to evoke the minimal useful evoked activity in a second location or region. With the clinical functional threshold the minimum stimulation amplitude (or combination of stimulation parameters) to start evoking clinical functions (e.g. muscle movements) is sought.

During surgery, the working stimulation amplitudes, waveforms, frequencies, pulse width and configurations and pulse trains are established. Establishing these parameters is appropriate for evoking of activity that is useful for the algorithms and methods described herein.

Stimulation takes place in multiple sites, whereby stimulation in these sites yields different evoked responses, albeit in some sites no evoking of activity occurs.

In an embodiment, the following method is used to establish stimulation parameters:
   a. establishment of threshold for evoking a clinical function (e.g. a motor or sensory activity); by for example stimulating from one of the sites known to be in appropriate motor/sensory area; or stimulating from all of the sites in order to see if there is one site that can evoke a clinical function. For example holding some of the parameters at a certain values and increasing/decreasing other parameter values until an evoked activity is detected and established
   b. Taking 70% (or other suitable factor) of that threshold and working with it during the evoking protocol.
   c. The threshold established will be a combination of frequency, number of pulses in trains, amplitude; pulse width, . . . etc.

A similar protocol from above is followed, but by establishment of threshold recorded activity response.

A more complete understanding of the components, processes, assemblies, and devices disclosed herein can be obtained by reference to the accompanying drawings. These figures (also referred to herein as "FIG.") are merely schematic representations (e.g., illustrations) based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Turning now to FIG. 1, an electrode carrying surgical drape constructed and operative, when the surgical drape is partially mounted on a head of a patient. Albeit the following description is focused on an exemplary embodiment where the surgical drape is mounted on the head of a patient, it should be appreciated that surgical drape constructed and operative as described herein may be similarly mounted on any other surgical area. An exemplary embodiment of a cranial surgical drape is illustrated and described throughout the disclosure, however it will be appreciated by a person skilled in the art that a sterility-maintaining surgical drape constructed as described and claimed herein may be applied in any other surgery and treatment site. A surgical drape comprises film 100 (that can be built also be laminated), which is mounted on a patient's head 102. Surgical drape 10 can generally be made of a resilient material, such as for example ductile polymeric film or alternatively weaved fabrics or weaved fabrics layered with wired electrodes. Film 100 can have two surfaces, first surface 104 can be fixed to patient's head 102, for example by adhesive applied to the entire first surface 104 or by adhesive applied to the perimeter of the first surface 104 of film 100 or using a tearable, peelable liner. First (or lower) surface 104 of film 100 may be fixed to patient's head 102 by means of any other suitable method. Second (or upper) surface 106 of film 100 can face the environment and can be provided for maintaining a sterile field of operation at the surgical site.

film 100 can generally be formed for example from a polyurethane material where every layer can have a thickness of, for example about 13 μm (0.005 inches). Different layers can have different thickness, for example, between about 8 μm and about 2000 μm. By way of example, and not by way of limitation, each layer may have a thickness of about 15 mils (0.015 inch, or about 0.375 mm) or less. Of course, embodiments of the surgical drape 10 that include film 100 of other thicknesses are also within the scope of the present technology. Alternate drape materials suitable for maintaining a sterile field may be used. Plurality of medical electrodes $108_p$ can be attached to film 100. Medical electrodes $108_p$ may be integrally formed with film 100, such as by printing of electrodes $108_p$ on film 100. Medical electrodes $108_p$ may alternatively be removably attached to film 100, such as by stitching, applying an adhesive or in any other suitable manner. Any kind of medical electrodes $108_p$ may be used in the surgical drapes described herein. For example, in an embodiment, EEG electrodes are used, however any kind of medical electrodes $108_p$ comprising conducting contacts, for obtaining various physiological characteristics of a patient may be used. For example, EMG, TES, EKG, ERP, EP, VEP, SSEP medical electrodes may be similarly used in accordance with an embodiment of the present invention.

Figure 2:
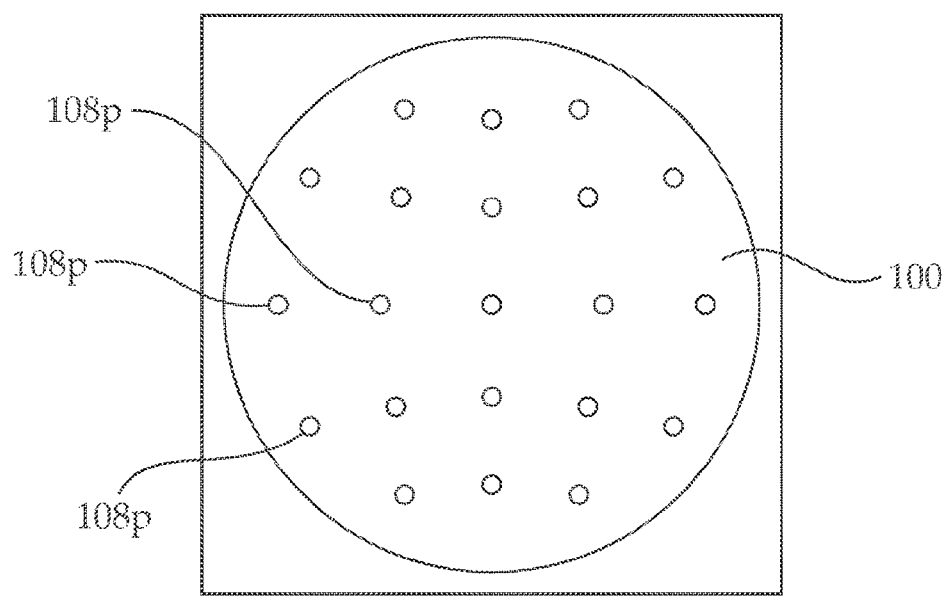
FIG. 2, illustrates an embodiment of an electrode carrying surgical drape, showing a first arrangement of electrodes over the surgical drape.
Figure 3:
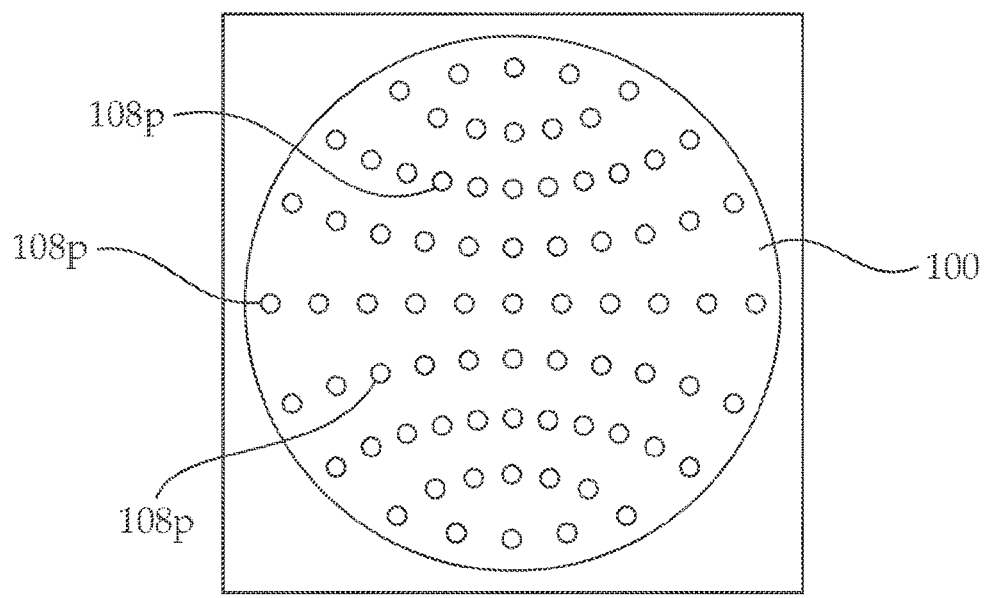
FIG. 3 illustrates another embodiment of an electrode carrying surgical drape, showing a second arrangement of electrodes over the surgical drape.
Figure 4:
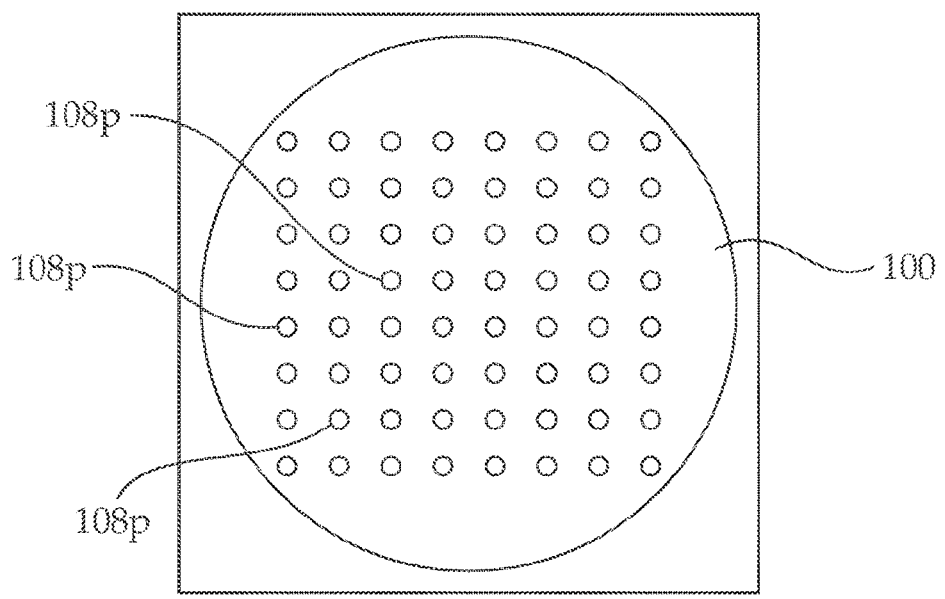
FIG. 4, illustrates an embodiment of an electrode carrying surgical drape, showing a third arrangement of electrodes over the surgical drape.

Reference is now made to FIGS. 2-4, illustrating three exemplary arrangements of the plurality of medical electrodes $108_p$ over film 100. As seen in FIGS. 2-4, any number of (medical) electrodes $108_p$ may be attached or integrally formed with film 100. Medical electrodes $108_p$ may be positioned at any location over patient's head 102 for efficiently and reliably obtaining patient's physiological characteristics from the readings provided by the plurality of medical electrodes $108_p$.

Figure 5:
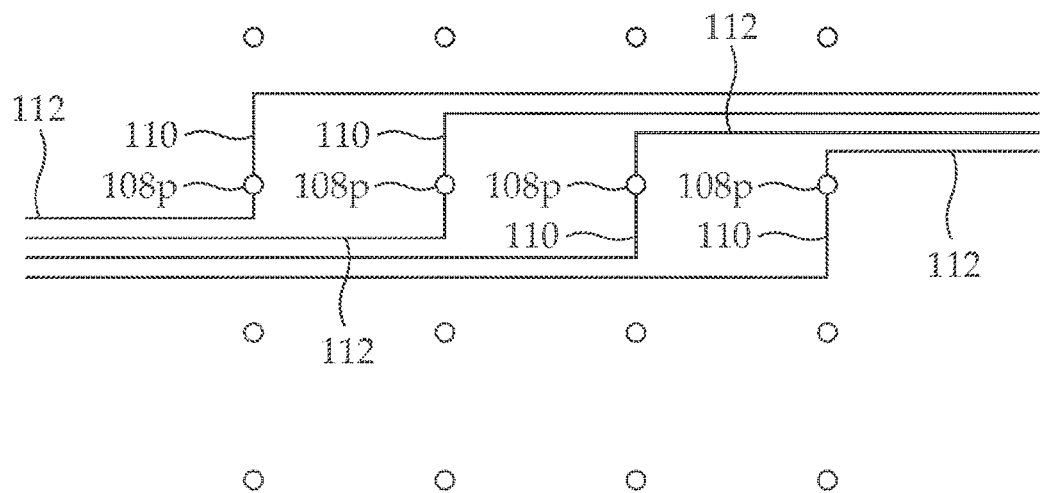
FIG. 5 illustrates a first arrangement of electrical connections between the electrodes incorporated in the surgical drape.
Figure 6:
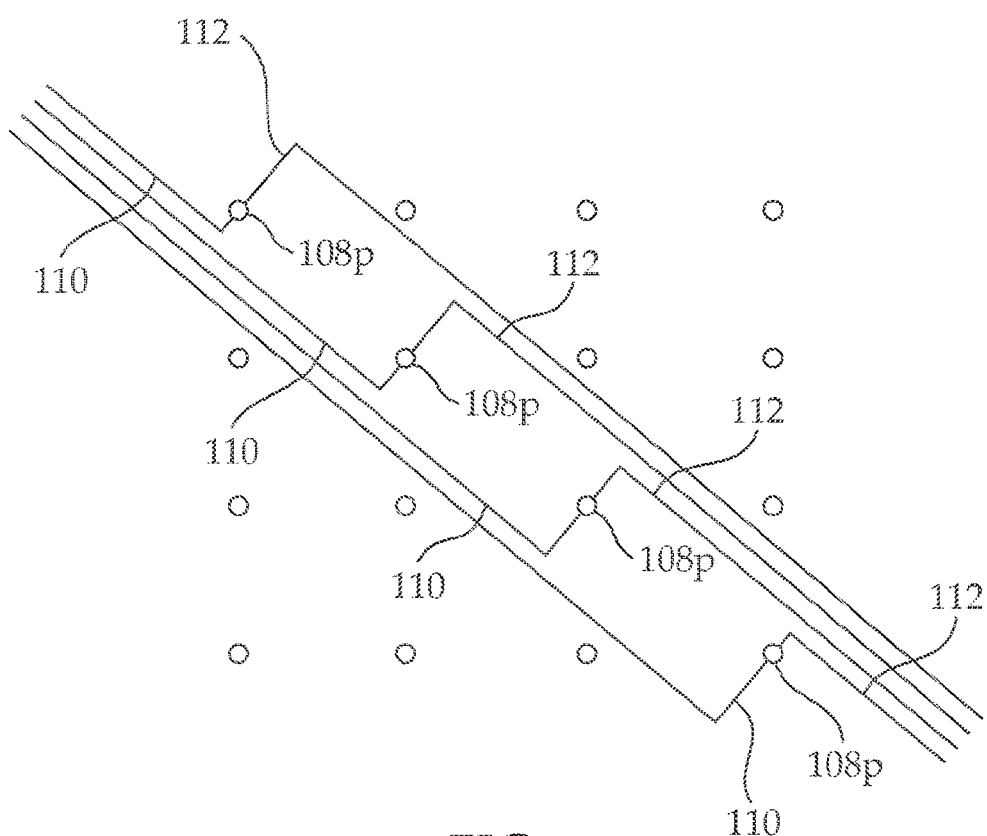
FIG. 6, illustrates a second arrangement of electrical connections between the electrodes incorporated in the surgical drape.

Reference is now made to FIGS. 5 & 6, which illustrate two exemplary different arrangements of electrical connections between medical electrodes $108_p$ incorporated in film 100. As illustrated, each of medical electrodes $108_p$ is provided with at least two electrical connection paths 110 and 112, which can be independently operative and configured to be connected to an electrical cable (not shown) for data transfer. If one of the electrical connection paths 110 or 112 is disconnected, the other one of connection paths 110 or 112 remains independently operative and enables continuous measurement of patient's physiological characteristics using the remaining operative electrical connection path 110 or 112.

As illustrated in FIG. 5, electrical connection paths 110 and 112 are positioned horizontally and extend in opposite ways from $p^{th}$ medical electrode $108_p$. Any other suitable method of arranging the plurality of medical electrodes $108_p$ may also be used. Similarly, in FIG. 6, electrical connection paths 110 and 112 are positioned diagonally and extend opposite ways from the $p^{th}$ medical electrode $108_p$. Any number of electrical connection paths may be provided to $p^{th}$ medical electrode $108_p$. For example, in case that medical electrode $108_p$ in a certain position is particularly important, more than two electrical connection paths may be provided thereto to ascertain that readings from this particular medical electrode $108_p$ are not impaired Reference is now made to FIGS. 7 & 8, illustrating the electrode carrying surgical drape having film 100, shown following fenestration of a surgical site within film 100 and a schematic illustration of electrical connection paths 110 and 112 between the medical electrodes $108_p$ incorporated in film 100.

Figure 7:
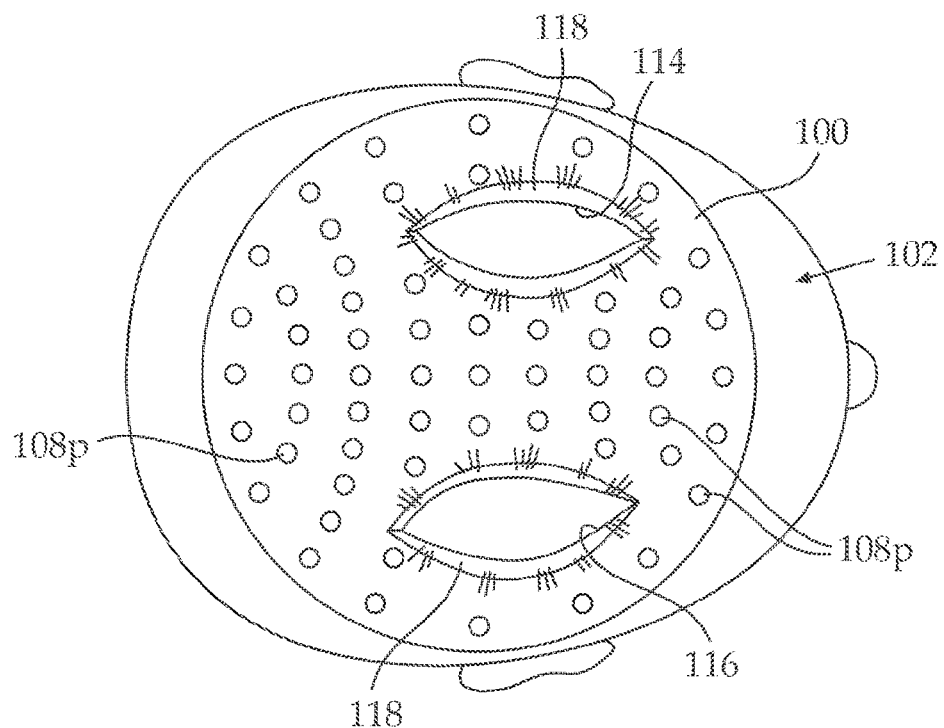
FIG. 7, is an illustration of the electrode carrying surgical drape, shown following fenestration of a surgical site within the surgical drape.

During a surgical procedure, film 100 can be cut (fenestration) in one or more locations in order to expose one or more surgical sites, such as 114 and 116 as shown in FIG. 7. Cutting of the electrode carrying surgical drape having film 100 along with the patient's skin and opening a surgical site usually forms skin fold 118, such that a portion of the second (upper) surface 106 of film 100 in the region of skin fold 118 faces the remainder of second surface 106 of film 100. As illustrated in FIG. 8 one of medical electrodes $108_p$ positioned adjacent surgical site 114 can have at least two electrical connection paths 110 and 112, whereas path 112 can be impaired during fenestrating for exposing surgical site 114 and electrical path 112 can likewise be disconnected as shown by section 120, however alternative electrical connection path 110 remains operative, thus medical electrode $108_p$ provides readings from a location adjacent surgical site 114. Another medical electrode $108_p$ can be positioned adjacent surgical site 114 and similarly can have two electrical connection paths 110 and 112, whereas path 110 of medical electrode $108_p$ can be impaired during cutting for exposing surgical site 114 and electrical path 110 can be disconnected as shown by section 120, however second alternative electrical connection path 112 remains operative, thus medical electrode $108_p$ can provide readings from a location adjacent surgical site 114.

Figure 8:
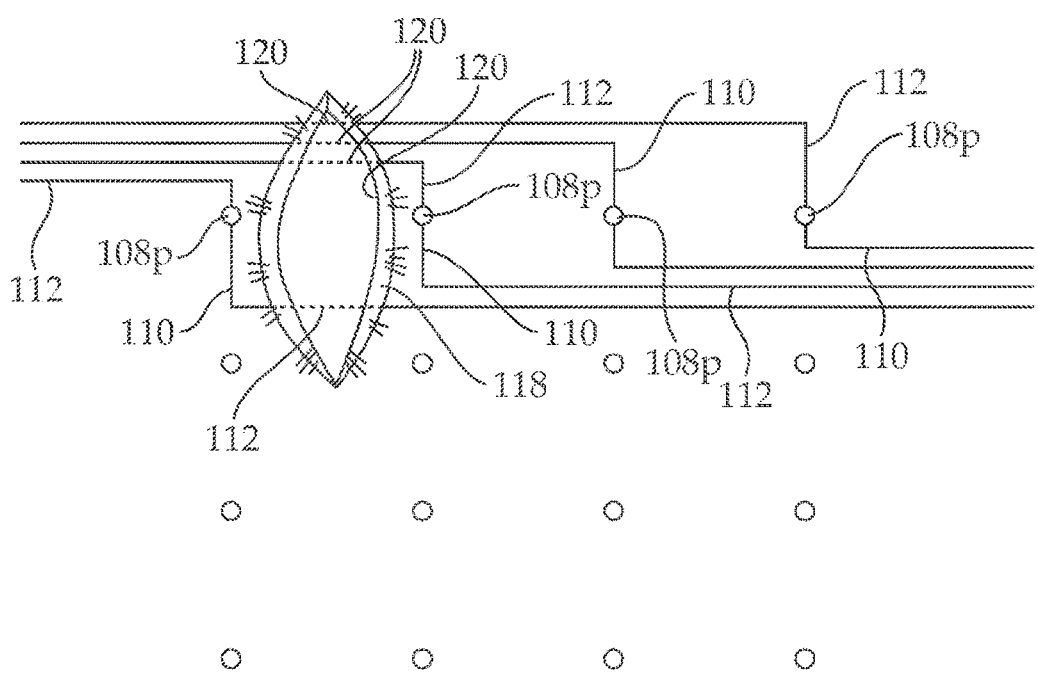
FIG. 8, illustrates electrical connections between the electrodes incorporated in the surgical drape following fenestration within the surgical drape.

Both medical electrodes $108_p$ shown in FIG. 8 can be located adjacent surgical site 114 and be capable of reliably providing readings of patient's physiological characteristics without compromising sterility of surgical site 114 because medical electrodes $108_p$ can be incorporate within film 100.

A stereotactic frame may be attached to patient's head 102 and thus mechanical co-registration of medical electrodes $108_p$ may be provided by assigning coordinate system to medical electrodes $108_p$ relative to the frame (not shown) and thus enabling a care provider to positively identify the readings of medical electrodes $108_p$ at any particular region of interest. Medical electrode $108_p$ can be placed on skin fold 118, in close proximity to patient's head 102 and identified using the abovementioned co-registration and be rendered inoperative in order to avoid inaccurate readings of medical electrode $108_p$ that cannot be positioned on patient's head 102 anymore. Medical electrodes $108_p$ may include a marker that can be identified by different methods, such as magnetic, ultrasonic or visual detection. Electrical connection paths 110 and 112 between medical electrodes $108_p$ can have a relatively large surface area, such that electrical connection paths 110 and 112 substantially fill the entire surface of the film 100. Thus, at least a portion of the electrical connection paths 110 and 112 remains operative following fenestration performed through film 100.

Figure 9:
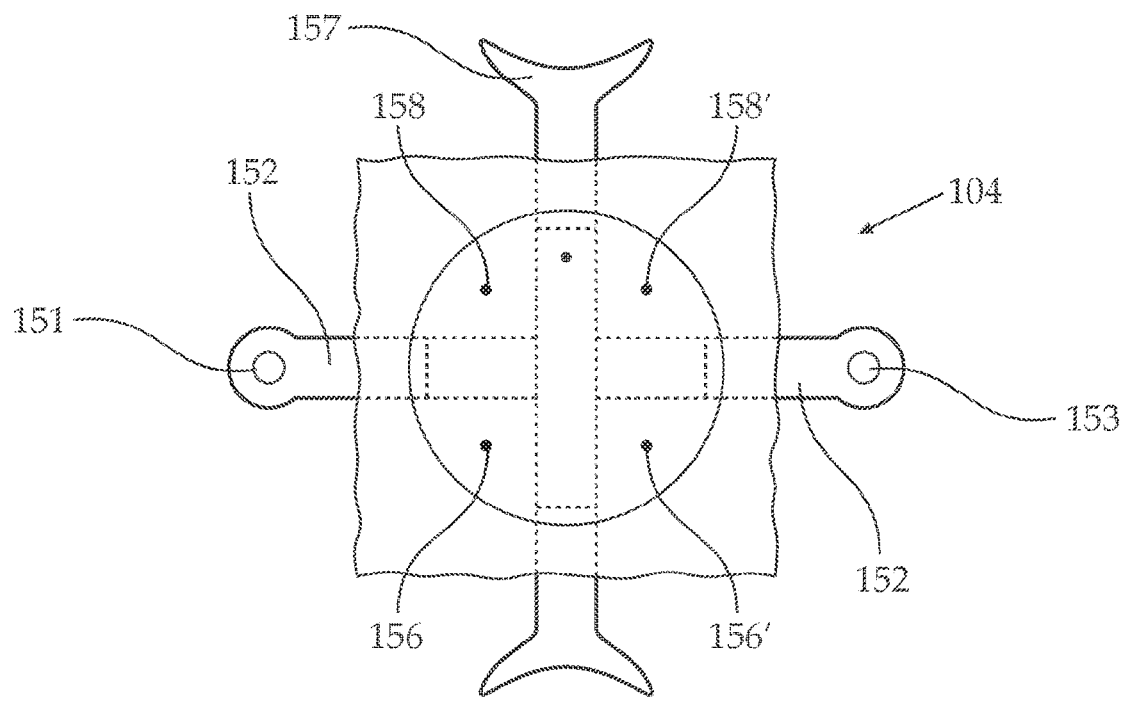
FIG. 9, illustrates the upper side of another embodiment of the drape (sterile side) with four locator extensions drawn.
Figure 10:
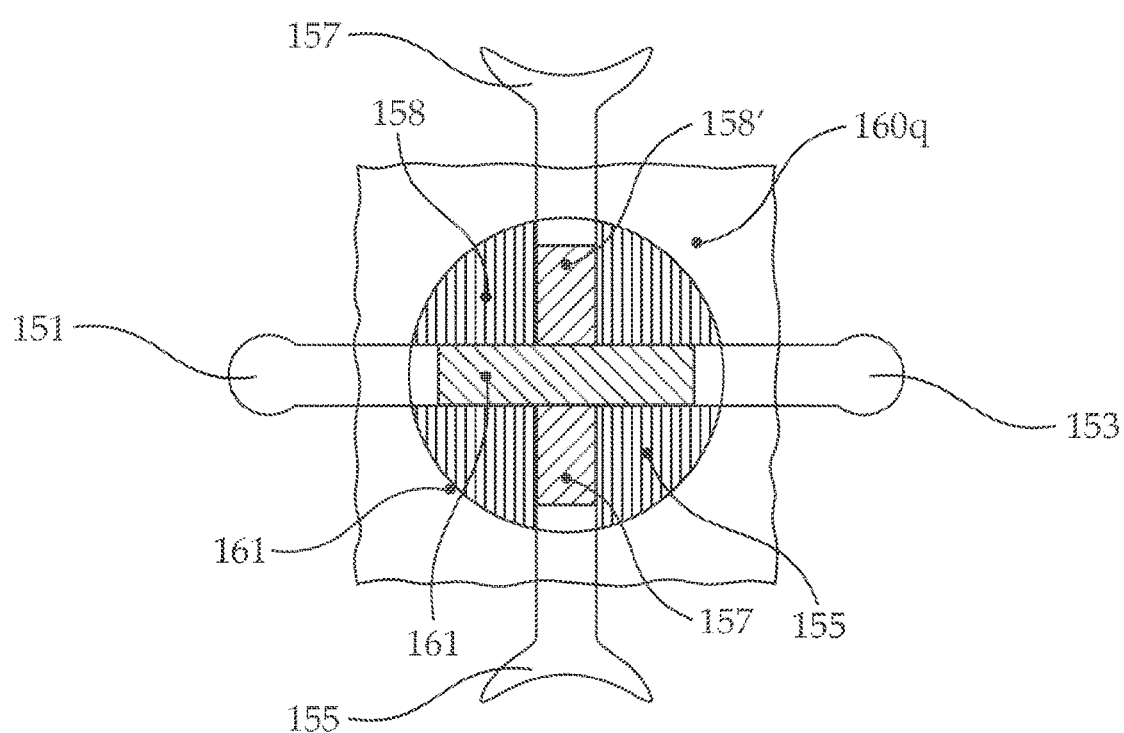
FIG. 10, illustrates the lower side of the embodiment illustrated in FIG. 9.

Turning now to FIGS. 9-12, illustrating the possible markings on surgical drape (that could also be resilient). As shown in FIG. 9, upper surface 106 of film 100 can further comprise posterior locator 151 coupled to upper surface 106 or lower surface 104 via strip 152, configure to extend from upper surface 106 or lower surface area 104, anterior locator 153 coupled to upper surface 106 or lower surface 104 via strip 154, configured to extend beyond upper surface 106 or lower surface area 104 configured to be positioned along a nasion-inion line of the patient's head 102 (not shown see e.g., FIG. 1). Likewise, upper surface 106 of film 100 can further comprise lateral right locator 155 coupled to the upper surface or lower surface via strings 156, 156', configured to extend beyond the upper surface 106 or lower surface area 104, left lateral locator 157 coupled to upper surface 106 or lower surface area 104 whereby for example strings 159, 159', can be used to facilitate the extension of lateral locator 157, configured to extend from upper surface 106 or lower surface area 104 and be positioned perpendicular to the nasion-inion line of subject's head 102 and along line connecting the right and left preauricular points (not shown). Conversely, FIG. 10 illustrates lower surface 104 of the drape, which will eventually face the scalp and expose electrode contacts $108_p$; extensions 151, 153, 155, and 157; strings 156. 156' and 158, 158' used to peel off liners 152, 154, and expose adhesive layer 161 and liners $160_q$ are shown in addition. Extensions 151, 153, 155 and 157 may have at least an adhesive layer separated by a peelable liner (Not shown) and be configured to adhere to the subject's scalp following extension. Surgical drape 10 may have at least a portion thereof that is transparent and be stretched to fit various head sizes of a patient following exposure of an adhesive layer such that anchoring one locator on one point, for example left preauricular point, will allow the formation of a helmet. The adhesive layer may be exposed beyond the strips associated with the locators, to allow a closer contact between the drape and the scalp. Likewise the location of the electrodes can be exposed, allowing the physician to determine where to make fenestration that will be the most effective.

Figure 11:
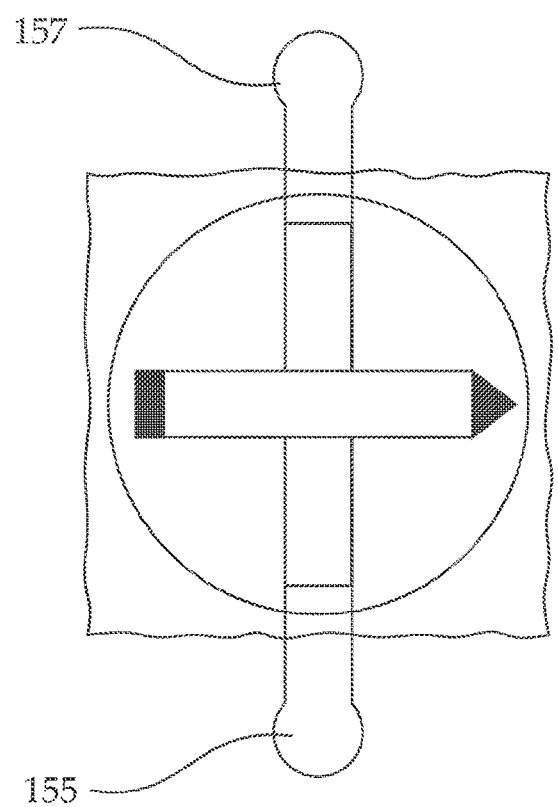
FIG. 11, illustrates an embodiment of the drape showing sterile drape with nasion and inion landmark anchoring positions (locators) are marked on the drape; while the left and right locators are anchored through extensions from the drape.
Figure 12:
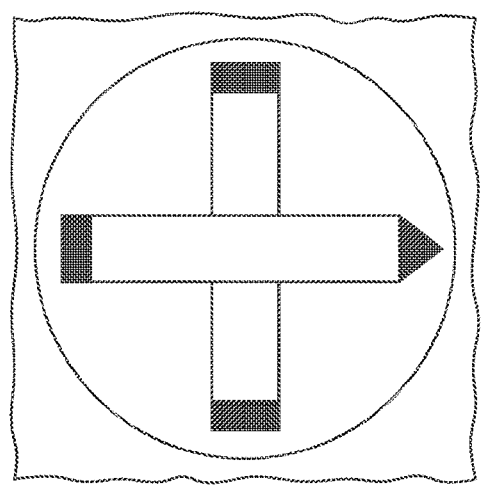
FIG. 12 illustrates an embodiment of the drape with markings (or scoring) on the drape specifying the positions of the locators on the drape.

FIGS. 11 and 12, shows other alternatives, whereby the inion-nasion line is graphically shown (FIG. 11) on surgical drape 10, while right 155 and left 157 lateral locators are extended beyond lower surface 104 and where both are graphically illustrated on upper surface 106. Although only graphically shown, the lines can form a peelable strip that is tearable to expose adhesive layer 161.

Figure 13:
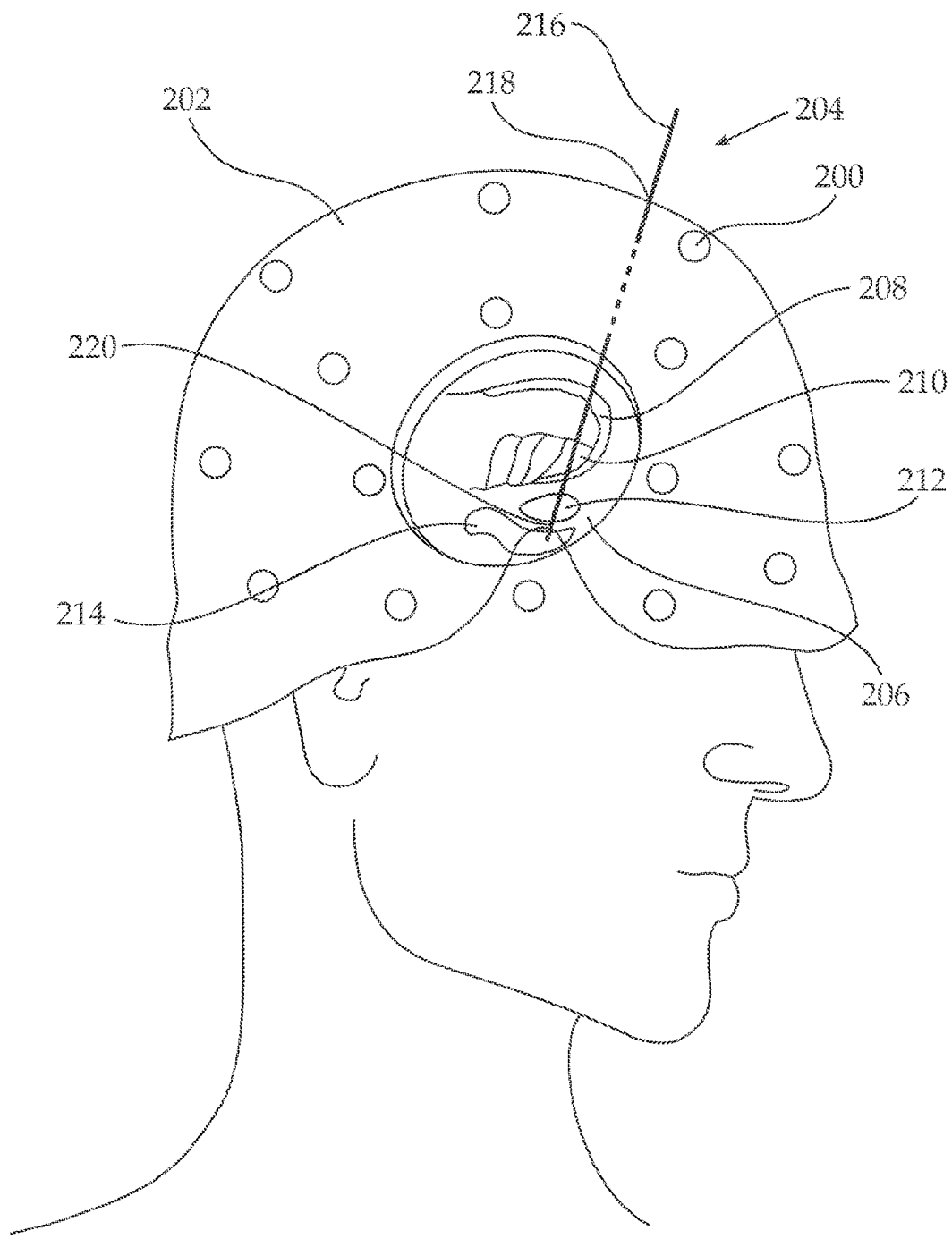
FIG. 13 illustrates a patient's head showing the placement of a probe into the brain.

Turning now to FIG. 13, illustrating a patient's head showing the placement of a brain probe into the brain. A plurality of fiducials 200, such as bolts or screws, are placed on a patient's head 102 in order to identify anatomical markings obtained by various imaging techniques, such as MRI for example. A brain probe 204 is inserted into patients' brain, designated by reference numeral 206. It is seen that the brain probe 204 extends through a plurality of brain regions, in this particular example through four different regions, 208, 210, 212 and 214. The electrodes of brain probe 204 are preferably mechanically or electronically co-registered with different brain regions. The brain probe 204 typically has a proximal portion 216, which is positioned close to the entry point 218 at the scalp of the patient and a distal portion 220, which is inserted into the brain 206. There is a relatively small amount of electrodes 204 at the proximal portion 216 of brain probe 204 and relatively large amount of electrodes (or contacts) at the distal portion 220 of the brain probe 204, which allows for high accuracy at a target area. For example, while performing a DBS surgery on awake patient, brain probe 204 is either incrementally advanced through different regions in brain 206 or inserted to the approximate target area at once and physiological response of the patient is measured for positioning brain probe 204 in the desired target area.

Figure 14:
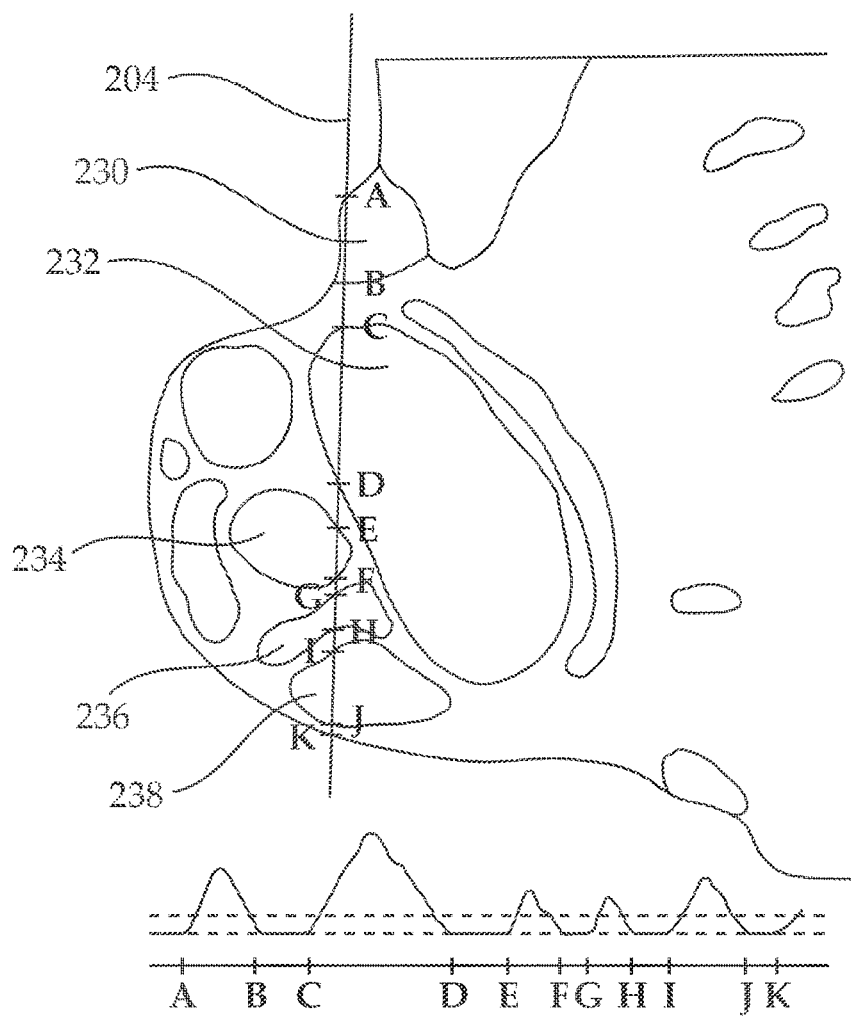
FIG. 14, illustrates entry and exit points to and from different brain regions.

Reference is now made to FIG. 14, showing entry and exit points to and from different brain 206 regions. The recorded evoked physiological responses along the path of brain probe 204 are analyzed. A plurality of parameters such as RMS, normalized RMS, power density of different frequency bands, firing rates, inter spike intervals or combination of the different parameters are identified. At least one of the following parameter reduction methods is employed: spiking firing rate; spiking amplitude and value; threshold crossing; power density bands of the recorded signal; RMS of background noise or signals; local/global minimums or maximums; principal components analysis or combination of parameters from. Statistical evaluation is performed in order to identify different segments of the brain 206. As shown in FIG. 14, brain probe 204 is either fully inserted into brain 206 or incrementally advanced through first region 230, which has an entry point A and an exit point B, second region 232, which has an entry point C and an exit point D, third region 234, which has an entry point E and exit point F, fourth region 236, which has an entry point G and exit point H and fifth region 238, which has an entry point I and exit point J. In an embodiment where brain probe 204 is used both as MES and MER, brain probe 204 is advanced through brain regions 230-238, while stimulating these brain regions and recording the resulting evoked physiological responses. A plurality of parameters is analyzed along the path of brain probe 204 and the exemplary graph shown in FIG. 14 is obtained, which represents the statistical analysis of characteristic transition points between the different brain regions.

Figure 15A:
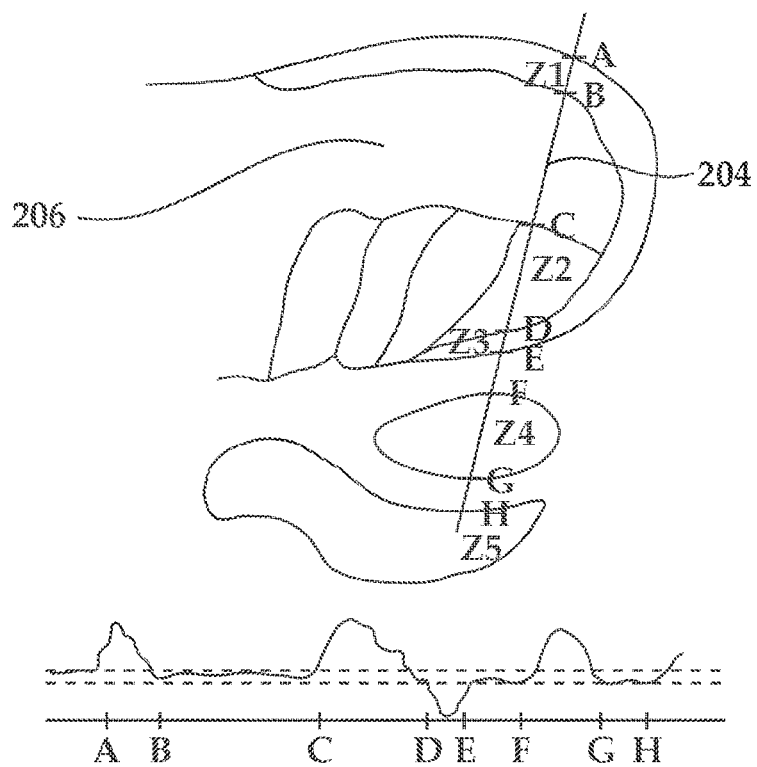
FIG. 15, shows an illustration (FIG. 15A) and a graph (FIG. 15B) of exemplary segmentation of the brain into different physiologically-active brain regions.
Figure 15B:
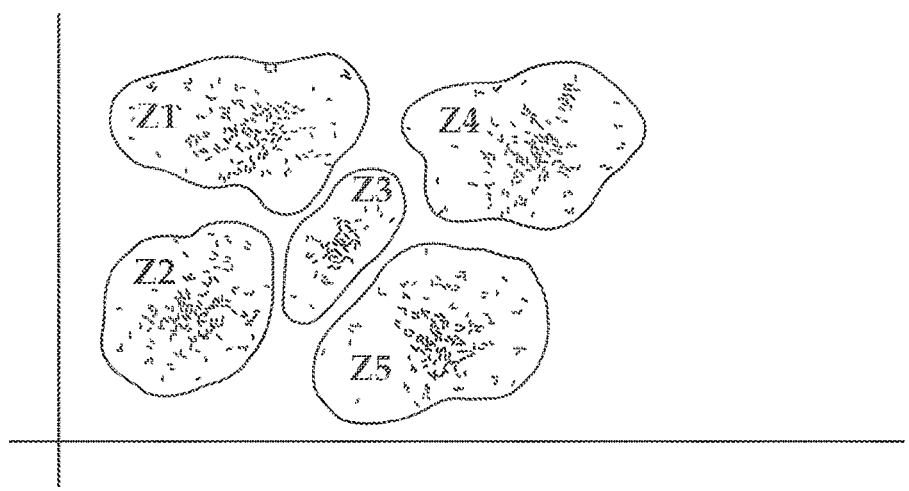

Turning now to FIG. 15, showing an illustration (FIG. 15A) and a graph (FIG. 15B) of exemplary segmentation of the brain into different physiologically-active brain regions. As shown (FIG. 15A) brain probe 204 is advanced through Zone 1, having entry point A and exit point B, Zone 2 Having entry point C and exit point D, Zone 3 having entry point D and exit point E, Zone 4 having entry point F and exit point G and Zone 5 having entry point H. A plurality of parameters such as RMS, Normalized RMS, power density of different frequency bands, firing rates, inter spike intervals or combination of the different parameters is analyzed along the path of the brain probe 204 and an exemplary graph in 15B is obtained, representing statistical analysis of the characteristic parameters for each of the different zones 1-5 of brain 206. The analyzing module can be configured to reduce or transform certain parameters from the recorded readings of evoked physiological responses in order to identify what is the threshold of brain stimulation that produces therapeutic effect.

Figure 16:
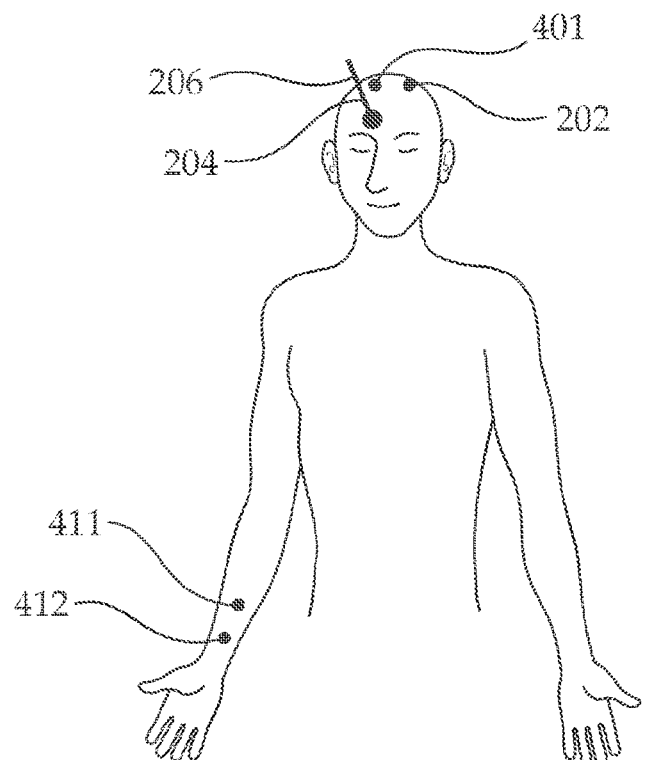
FIG. 16, illustrates an embodiment for configuring location of the macro-electrodes mapping for mapping physiologically active brain regions.
Figure 17:
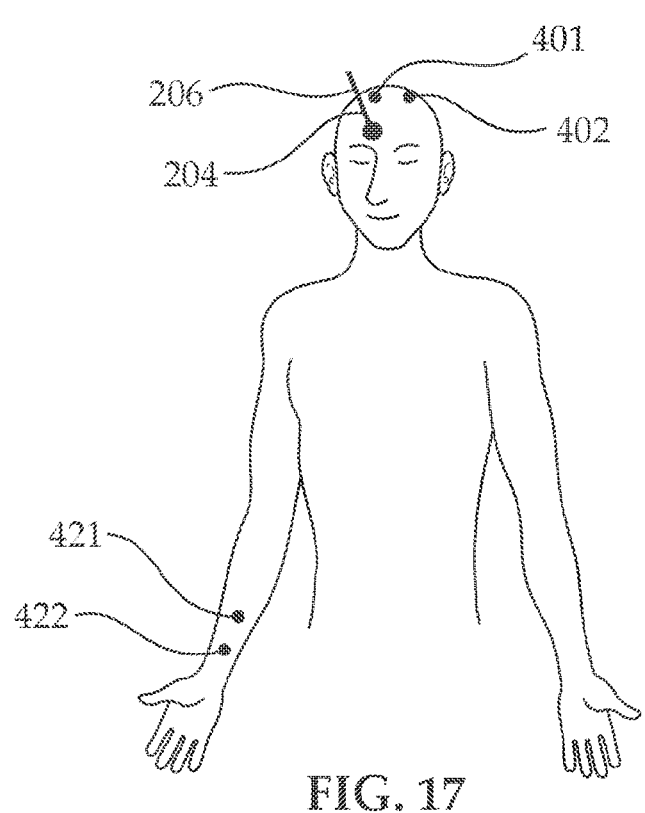
FIG. 17, illustrates another embodiment for configuring location of the macro-electrodes mapping for mapping physiologically active brain regions.

Turning now to FIG. 16, illustrating an embodiment for the use of the brain mapping systems described herein in conjunction with intraoperative monitoring (IOM) tools (e.g., SEP, VEP, AEP, MEP, etc.). Mapping thus is carried out by contacting the plurality of physiologically functional brain regions with at least one probe and stimulating the plurality of regions through the probe contacts in the different regions in the brain; while simultaneously standard intraoperative monitoring tools are activated to measure the effect of stimulation on the established IOM responses and thus determine where exactly the brain stimulating electrode contacts are. The systems described herein can be used in an embodiment for mapping functional brain region and an example is illustrated in FIG. 16. As shown in FIG. 16 stimulating electrodes 411 and 412 are used to evoke a response in the median nerve and the response can be measured using, for example, cranial EEG electrodes in locations 401, 402 (for example, using the surgical drape described herein, fenestrated in locations 401, 402). Recording of the evoked response from locations 411, 412 establishes a baseline and can be done in both awake and sedated subject. Using probe 204, for example, the probe shown in FIG. 20, probe 204 is inserted to the subject brain and various regions of interest can then be subject to, for example, localized stimulation or non-localized stimulation, and the effect of the stimulation on the established evoked potential baseline can then be evaluated thereby facilitating mapping of functional brain region. The evoked potential baseline established can be, for example: Somatosensory evoked potentials (SEPs or SSEPs), or Visual-evoked potentials (VEPs) tracking visual signals from the retina to the occipital cortex. Other examples can be motor-evoked potential (MEP) and Auditory Evoked Potential (AEP). Accordingly, one could establish a baseline; absent stimulation using probe 204, followed by localized or non-localized stimulation. The effect of the probe on the baseline could be on prohibiting of the EPs or on latency or amplitude of EPs; or even waveform shape. Likewise, FIG. 17 shows the reverse condition, where stimulation can be performed using probe 204 for macro-depth stimulation, together with cortical stimulation in points 401, 402, while using, for example, remotely positioned electromyography (EMG) electrodes in points 421, 422 to record MEP, following establishing of the baseline.

Figure 18A:
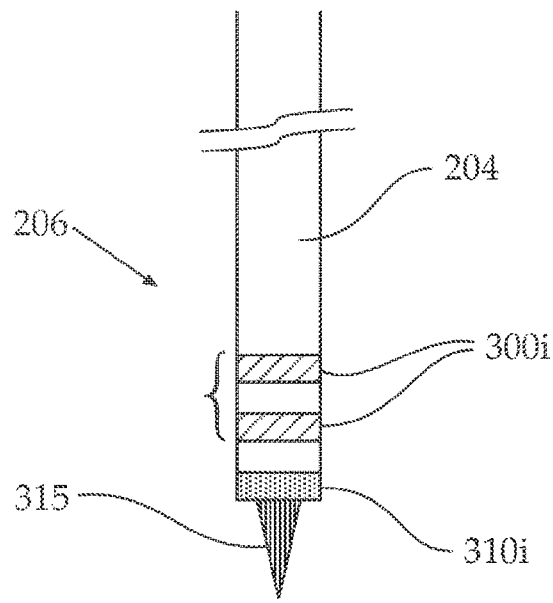
FIG. 18, illustrates an embodiment of the spatial arrangement of the electrodes on the probe with a micro-contact tip (FIG. 18A), and without a micro contact tip (FIG. 18B)
Figure 18B:
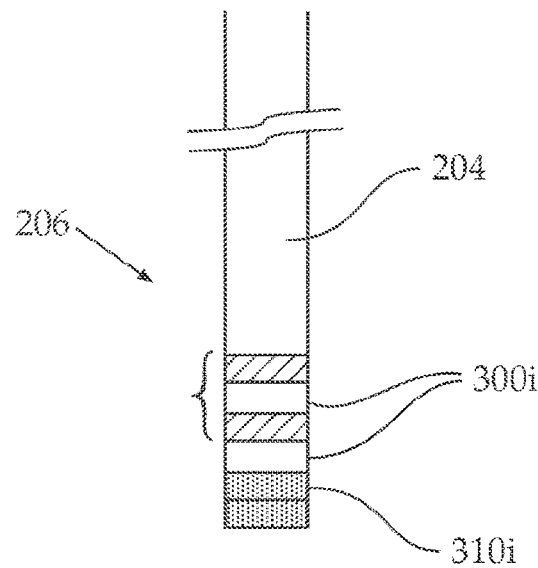
Figure 19:
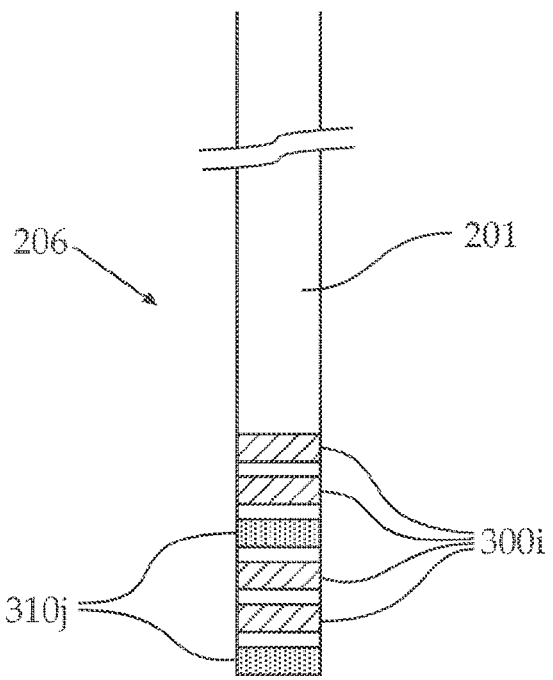
FIG. 19, illustrates an embodiment of the spatial arrangement of the electrodes on the macro-electrode.
Figure 20:
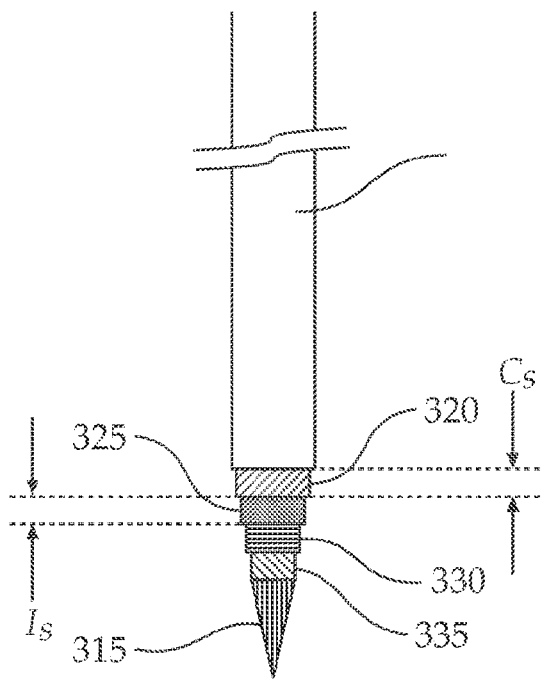
FIG. 20 illustrates a probe with two macro contacts that can be used for test stimulation if stimulated together, or for evoked electrophysiology if stimulated unipolar or bipolar.

FIGS. 18-20 illustrates embodiments of brain probe 204 configuration of contacts or electrodes $300_i$ (recording and/or stimulating contacts/electrodes), electrodes $310_j$ (test-stimulation electrodes/contacts) and micro tip electrode 315. FIG. 18 illustrates brain probe 204 with macro contact $310_j$ used for example, for test stimulation as well as other more miniature macro contacts $300_i$ to be used for the evoked stimulation, these can be used in unipolar or bipolar stimulation configurations. As shown in FIG. 18A, brain probe can comprise micro electrode 315 used for recording; while in FIG. 18B the brain probe does not use that micro-tip 315.

As shown in FIG. 19, there are a number of brain probe 204 ring contacts (at least 2); they can be stimulated together in order to supply test stimulation (stimulation mapping) functionality; but also they can be stimulated separately for localized bipolar evoked stimulation or a more localized stimulation by stimulating from one contact and returning current bipolar from an adjacent contact.

Turning now to FIG. 20, illustrating probe 204 with two macro contacts 320, 330 also used for test stimulation if stimulated together, or for evoked electrophysiology if stimulated unipolar or bipolar. The distance between the contacts can have substantial importance over the effectiveness of the evoking ability of contacts 320 and 330. As shown in FIG. 20, micro-tip 315 can be retractable and be either exposed or covered. The brain probe in FIG. 20, can be formed of alternating, telescopic concentric tubes of conducting and insulating material, The contact surface of macro ring contacts 320, 330 can be selectively regulated by aligning insulating tubes 325, 335 and conducting tubes 320, 330. Similar arrangement can be made for macro-electrodes illustrated in FIGS. 18A, 18B and 19. Several possibilities can exist for activation within evoked or non-evoked protocols: these can be for example; performing localised stimulation by stimulating between macro contacts 320 and macro-contact 330. For example, the distance between macro contact 320 and 330 can be varied (e.g., during production or mechanically during the probe operation) by extending the insulation tube covering conducting tube 330. Due to insulation, polarity can also be selected to provide bipolar stimulation along the whole length of insulating tube 335; distance between the macro contact 330 and 320 can also be setup according to the region of interest size; Recording evoked/non-evoked differential LFP (local field potential) between macro contacts 320 and macro-contact 330 (one contact, e,g, 320 can be a reference to contact 330), or performing test stimulation for the establishment of a therapeutically effective window by electrically shortening both macro contacts 320 and macro-contact 330 and stimulating through them, this can be for example achieved by a system of switches that switches the electrode between the different modes of operation to obtain the necessary evoked response signals. Also shown in FIG. 20, are probe housing 350 and contact span ($C_S$), referring to the longitudinal thickness of the conducting area of the electrode 320. It stands to reason, that any conducting surface, for example $300_i$ in FIG. 19, or macro-contact 330 in FIG. 20, will similarly have a conducting span ($C_S$). Likewise, non-conducting surface of probe 204 which, in an embodiment, can be insulating tube 325, or the gap between adjacent contacts $300i$ and $310j$ in FIGS. 18 (A,B) and 19, can have longitudinal span ($I_S$).

One or more components may be referred to herein as "configured to," "configured by," "configurable to," "operable/operative to," "adapted/adaptable," "able to," "conformable/conformed to," etc. The terms (e.g. "configured to") can generally encompass active-state components and/or inactive-state components and/or standby-state components, unless context requires otherwise.

While in the foregoing specification the surgical cranial drape, microelectrodes for mapping brain of a subject and their methods of use have been described in relation to certain preferred embodiments, and many details are set forth for purpose of illustration, it will be apparent to those skilled in the art that the disclosure of the surgical cranial drape, microelectrodes for mapping brain of a subject and their methods of use are susceptible to additional embodiments and that certain of the details described in this specification and as are more fully delineated in the following claims can be varied considerably without departing from the basic principles of this invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:
1. A therapeutic effect assessment system, comprising:
a. a deep brain stimulation (DBS) probe shaped and sized to be inserted into a brain of a subject, having a proximal end and a distal end and a longitudinal axis, the probe comprising a plurality of contacts operably coupled thereto, disposed along the longitudinal axis, wherein said DBS probe is selectively operable for stimulating electrophysiological evoked responses, and for delivery of a DBS treatment using at least two contacts disposed along the longitudinal axis of said DBS probe;
b. at least one electrode configured to record brain electrical signals generated in response to said stimulated electrophysiological evoked responses caused by said stimulating; and
c. an analysis module electrically connected to said probe and to said at least one electrode, wherein said analysis module is configured to transform or reduce certain parameters from the recorded brain electrical signals generated in response to said electrophysiological evoked responses caused by said stimulating using said at least two contacts using a stimulation threshold, in order to identify a clinical therapeutic threshold of brain stimulation that produces a clinical therapeutic effect of said DBS treatment when using said at least two contacts;
wherein said analysis module is further configured for mapping functional brain regions along an insertion path of said DBS probe;
identifying a motor or a sensory brain region along said insertion path based on said mapping;
wherein said stimulating comprises stimulating said identified motor or sensory brain region using said stimulation threshold using said at least two contacts of said DBS probe.

2. A system according to claim 1, wherein said certain parameters comprise one or more of RMS, Normalized RMS, power density of different frequency bands, firing rates, and inter spike intervals.

3. A system according to claim 1, wherein said system is operative for providing segmentation of the brain into a plurality of physiologically active brain regions based on signals recorded by said at least one electrode.

4. A system according to claim 1, wherein said at least one electrode is positioned on said DBS probe.

5. A system according to claim 1, wherein stimulating electrophysiological evoked response comprises stimulating unipolar signal, bipolar signal or both unipolar and a bipolar signal, and wherein said recording said brain electrical signals comprises recording single ended signal, or differential signal.

6. A system according to claim 1, wherein at least two of the plurality of contacts of said first probe are macro-contacts configured to selectively perform localized stimulation.

7. A system according to claim 6, wherein localized stimulation is configured to take place between two adjacent macro-contacts of said first probe.

8. A system according to claim 1, wherein said analysis module is operative for providing segmentation of the brain into a plurality of physiologically active brain regions based on said brain electrical signals recorded by said at least one electrode.

9. A system according to claim 1, wherein said probe is shaped as a needle.

10. A system according to claim 1, wherein said analysis module is configured to transform or reduce certain parameters from the recorded brain electrical signals in order to establish a clinical therapeutically effective window of said DBS treatment.

11. A system according to claim 1, wherein said brain electrical signals recorded by said at least one electrode comprise readings of brain evoked responses generated in response to said stimulated electrophysiological evoked responses using said stimulation threshold.

12. A method for assessing a therapeutic effect of brain stimulation in a subject, comprising:
inserting the DBS probe of claim 1 along an insertion path into the brain of a subject;
stimulating a brain region at a first location using a stimulation threshold using at least two contacts of said DBS probe disposed along the longitudinal axis of the DBS probe, in a manner suitable to evoke an electrophysiological response;
recording in a second location brain electrical signals generated in response to said stimulated electrophysiological evoked responses caused by said stimulating;
analyzing the recorded electrical signals;
identifying a clinical therapeutic threshold of brain stimulation that establishes a clinical therapeutically effective window of said DBS treatment when using said at least two contacts for delivery of said DBS treatment, based on said analysis results;
wherein said method further comprises mapping functional brain regions along said insertion path of said DBS probe;
identifying a motor or a sensory brain region along said insertion path based on said mapping;
wherein said stimulating comprises stimulating said identified motor or sensory brain region using said stimulation threshold using said at least two contacts of said DBS probe.

13. A method according to claim 12, wherein said analyzing comprises reducing or transforming certain parameters from said recorded brain electrical signals.

14. A method according to claim 12, wherein said brain electrical signals recorded in said second location comprise readings of a brain evoked electrophysiological response.

* * * * *